(12) United States Patent
Maris et al.

(10) Patent No.: US 8,567,253 B2
(45) Date of Patent: *Oct. 29, 2013

(54) OPTO-ACOUSTIC METHODS AND APPARATUS FOR PERFORMING HIGH RESOLUTION ACOUSTIC IMAGING AND OTHER SAMPLE PROBING AND MODIFICATION OPERATIONS

(75) Inventors: Humphrey J. Maris, Barrington, RI (US); Arto V. Nurmikko, Providence, RI (US)

(73) Assignee: Brown University, Providence, RI (US)

( * ) Notice: Subject to any disclaimer, the term of this patent is extended or adjusted under 35 U.S.C. 154(b) by 1184 days.

This patent is subject to a terminal disclaimer.

(21) Appl. No.: 11/921,635

(22) PCT Filed: May 30, 2006

(86) PCT No.: PCT/US2006/020952
§ 371 (c)(1),
(2), (4) Date: May 7, 2009

(87) PCT Pub. No.: WO2006/132862
PCT Pub. Date: Dec. 14, 2006

(65) Prior Publication Data
US 2009/0272191 A1 Nov. 5, 2009

Related U.S. Application Data

(63) Continuation of application No. 11/274,628, filed on Nov. 14, 2005, now abandoned, and a continuation of application No. 11/324,866, filed on Jan. 4, 2006, now Pat. No. 7,624,640.

(60) Provisional application No. 60/687,070, filed on Jun. 3, 2005.

(51) Int. Cl.
*G01N 29/34* (2006.01)
*G01N 29/06* (2006.01)

(52) U.S. Cl.
USPC .............................................. 73/643; 73/642

(58) Field of Classification Search
USPC ..................................................... 73/643, 642
See application file for complete search history.

(56) References Cited

U.S. PATENT DOCUMENTS

| 4,137,991 A | 2/1979 | Melcher et al. ................ 181/142 |
| 4,267,732 A | 5/1981 | Quate ............................. 73/606 |

(Continued)

FOREIGN PATENT DOCUMENTS

JP  10-128236 A  5/1998

OTHER PUBLICATIONS

R.A. Lemons and C.F. Quate, "Acoustic Microscope—Scanning Version", Applied Physics Letters, vol. 24, No. 4, Feb. 15, 1974.

B. Hadiomioglu and C.F. Quate, "Water acoustic microscopy at suboptical wavelengths", Applied Physics Letter 43 (11), Dec. 1, 1983, pp. 1006-1007.

(Continued)

*Primary Examiner* — Peter Macchiarolo
*Assistant Examiner* — Rose M Miller
(74) *Attorney, Agent, or Firm* — Merchant & Gould P.C.

(57) ABSTRACT

An opto-acoustic transducer assembly includes a substrate; at least one layer of opto-acoustic material coupled to a surface of the substrate, where the at least one layer of opto-acoustic material generates sound waves when struck by pulses of pump light; and an acoustic lens configured to focus sound waves generated by the at least one layer of opto-acoustic material towards a sample. The acoustic lens is further configured to collect sound waves returning from the sample and to direct the returning sound waves to the at least one layer of opto-acoustic material. In one non-limiting embodiment the at least one layer of opto-acoustic material is interposed between the substrate and the acoustic lens, and the substrate is substantially transparent to light having wavelengths of interest.

87 Claims, 17 Drawing Sheets

(56) References Cited

U.S. PATENT DOCUMENTS

| | | | |
|---|---|---|---|
| 4,269,067 A | 5/1981 | Tynan et al. | 73/643 |
| 4,430,897 A | 2/1984 | Quate | 73/606 |
| 4,710,030 A | 12/1987 | Tauc et al. | 356/432 |
| 4,909,082 A | 3/1990 | Khuri-Yakub et al. | 73/642 |
| 4,938,216 A | 7/1990 | Lele | 128/399 |
| 5,431,055 A | 7/1995 | Takata et al. | 73/618 |
| 5,457,997 A | 10/1995 | Naruo et al. | 73/643 |
| 5,615,675 A | 4/1997 | O'Donnell et al. | 128/653.1 |
| 5,706,094 A | 1/1998 | Maris | 356/432 |
| 5,748,317 A | 5/1998 | Maris et al. | 356/357 |
| 5,748,318 A | 5/1998 | Maris et al. | 356/381 |
| 5,844,684 A | 12/1998 | Maris et al. | 356/432 |
| 5,864,393 A | 1/1999 | Maris | 356/28 |
| 5,999,847 A | 12/1999 | Elstrom | 604/20 |
| 6,025,918 A | 2/2000 | Maris | 356/388 |
| 6,038,026 A | 3/2000 | Maris | 356/357 |
| 6,317,216 B1 | 11/2001 | Maris | 356/496 |
| 6,321,601 B1 | 11/2001 | Maris | 73/657 |
| 6,491,685 B2 | 12/2002 | Visuri et al. | 601/4 |
| 7,339,676 B2 | 3/2008 | Maris | 356/432 |
| 7,624,640 B2 | 12/2009 | Maris et al. | 73/643 |
| 7,782,471 B2 | 8/2010 | Maris | 356/630 |
| 7,935,107 B2 | 5/2011 | Altshuler et al. | 606/9 |
| 7,942,915 B2 | 5/2011 | Altshuler et al. | 607/88 |
| 7,942,916 B2 | 5/2011 | Altshuler et al. | 607/88 |
| 2001/0055435 A1 | 12/2001 | Biagi et al. | 385/7 |
| 2006/0272418 A1 | 12/2006 | Maris et al. | 73/606 |
| 2006/0272419 A1 | 12/2006 | Maris et al. | 73/606 |

OTHER PUBLICATIONS

A. Rodriguez Rey, G.A.D. Briggs, T.A. Field and M. Montoto, "Acoustic Microscopy of Rocks", Journal of Microscopy, vol. 160, Pt 1, Oct. 1990, pp. 21-29.

K. Yamanata and Y. Enomoto, "Observation of Surface Cracks with an Acoustic Microscope", Journal of Applied Physics 53 (2), Feb. 1982.

G. Tas, J.J. Loomis, H.J. Maris, A.A. Bailes, and L.E. Seiberling, "Picosecond Ultrasonics Study of the Modification of Interfacial Bonding by Ion Implantation", Applied Physics Letters, vol. 72, No. 18, pp. 2235-2237.

J. Bereiter Hahn, "Scanning acoustic microscopy visualizes cytomechanical responses to cytochalasin D", Journal of Microscopy, vol. 146, Pt 1, Apr. 1987, pp. 29-39.

E.A. Schenk, R.W. Waag, A.B. Schenk and J.P. Aubuchon "Acoustic microscopy of red blood cells", Journal of Histochemistry and Cytochemistry, vol. 36, No. 10, 1988, pp. 1341-1351.

J.A. Hildebrand and D. Rugar, "Measurement of cellular elastic properties by acoustic microscopy", Journal of Microscopy, vol. 134, Pt 3, Jun. 1984, pp. 245-260.

J. Wu, "Acoustical tweezers", J. Acoust. Soc. Am. 89 (5), May 1991, pp. 2140-2143.

V.I. Trigub and A.V. Plotnov, "A Change in the Structure of an Ultrasonically Processes MMA-MAA Based Photoresist", Technical Physics Letters, vol. 28, No. 6, 2002.

Y. Arata, Yue Chang Zhang; "Intense Sonoimplantation of atoms from gases into metals", Applied Physics Letters, vol. 80, No. 13, Apr. 1 2002, pp. 2416-2418.

I.V. Ostrovskii, L.P. Steblenko, A.B. Nadtochii, "Ultrasound-Induced Surface Hardening of Dislocation-Free Silicon", Atomic Structure and Nonelectronic Properties of Semiconductors, vol. 34, No. 3, Mar. 2000. pp. 251-254.

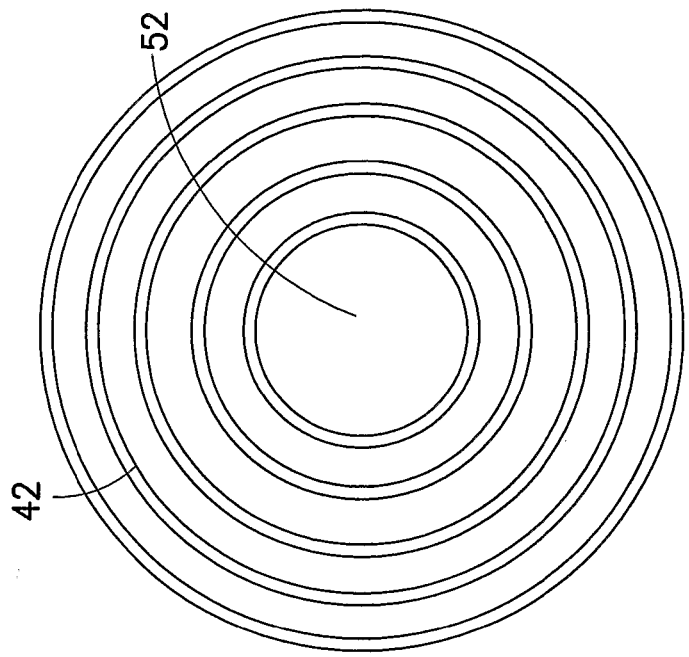
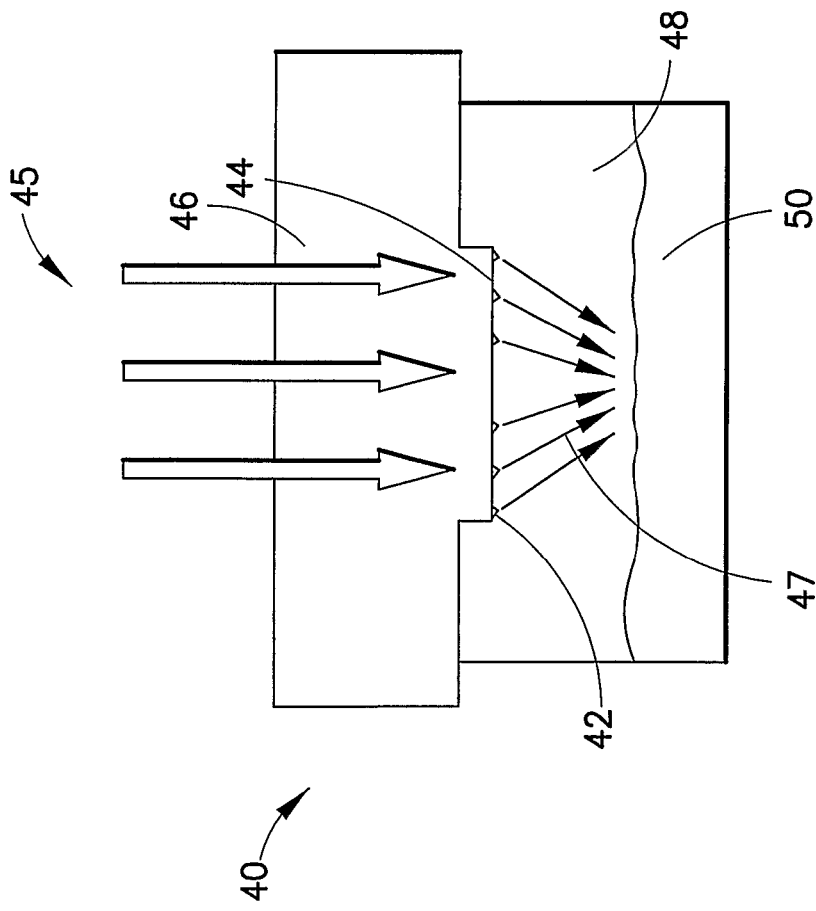
FIG. 2A
FIG. 2B
FIG. 2

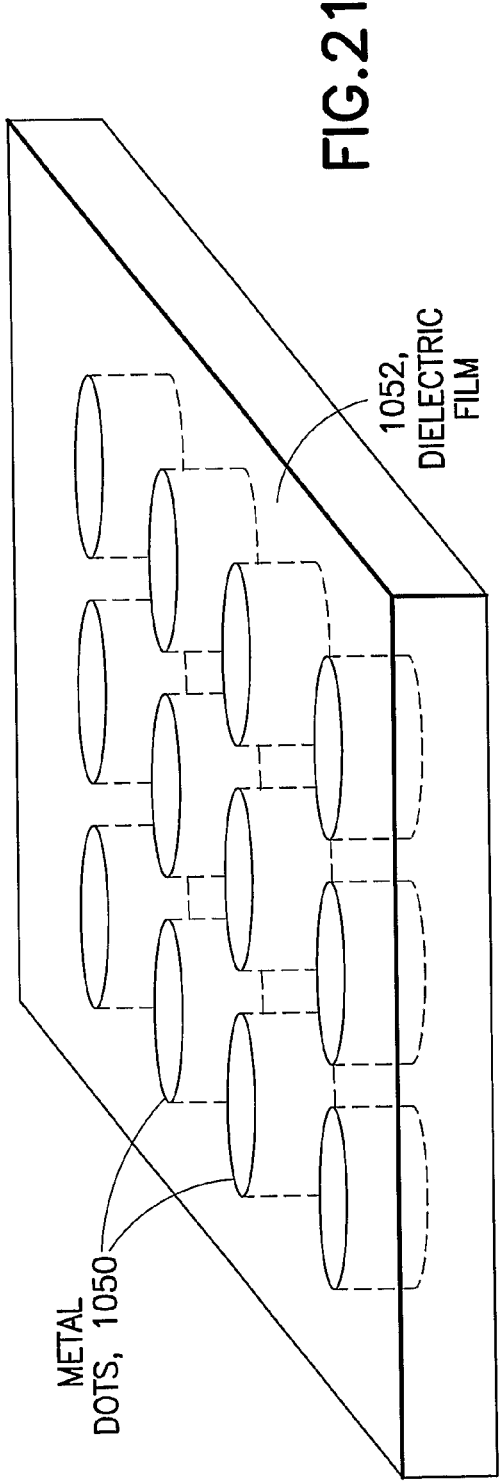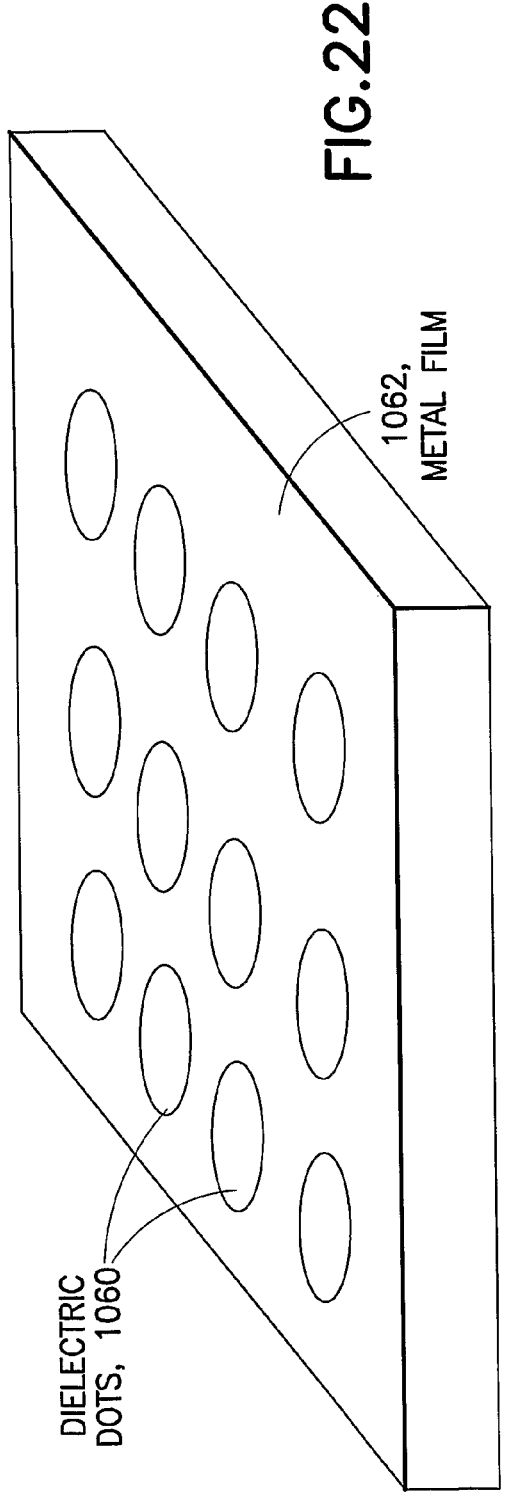

OPTO-ACOUSTIC METHODS AND APPARATUS FOR PERFORMING HIGH RESOLUTION ACOUSTIC IMAGING AND OTHER SAMPLE PROBING AND MODIFICATION OPERATIONS

CROSS REFERENCE TO RELATED APPLICATIONS

This application is a National Stage of and claims benefit to PCT/US06/20952 filed on May 30, 2006, which is a continuation of U.S. application Ser. No. 11/324,866 filed Jan. 4, 2006 and issued as U.S. Pat. No. 7,624,640 on Dec. 1, 2009, which is a continuation of U.S. application Ser. No. 11/274,628 filed Nov. 14, 2005, now abandoned, which claims benefit to U.S. Provisional Application Ser. No. 60/687,070 filed Jun. 3, 2005, the disclosures of which are hereby incorporated by reference in their entireties. To the extent appropriate, a claim of priority is made to each of the above disclosed applications.

TECHNICAL FIELD

The present invention generally concerns methods and apparatus suitable for use in instruments in which sound waves are used to perform imaging operations, and more particularly concerns instruments such as, for example, scanning acoustic microscopes, in which sound waves used to perform imaging and other sample probing operations are generated by an opto-acoustic process.

BACKGROUND

In an acoustic microscope sound is generated in some way and then brought to a focus. The object to be studied is placed at or near the focus and an image of the object is obtained by moving the object laterally and monitoring the variation of the amplitude and phase of the acoustic waves that are reflected from the object or that are transmitted through the object. Instead of moving the object that is to be imaged, it is often preferable to hold the object in one place and vary the position of the acoustic focus. The position of the acoustic focus can be changed by moving the position of the lens used to focus the sound.

Conventional acoustic microscopes consist of a transducer to generate sound, and a lens to focus the sound, a coupling medium (usually water) through which the sound propagates to come to a focus, and the sample object. The sound reflected from the object may be collected by the same lens that is used to focus the incident beam or by another lens. To collect sound transmitted through the sample a collection lens is needed on the far side of the sample.

It is usually considered that the first scanning acoustic microscope was built by R. A. Lemons and C. F. Quate, (see "Acoustic Microscope—Scanning Version", Appl. Phys. Lett. 24, 163 (1974)). This used a continuous acoustic wave of frequency 160 MHz, had a resolution of 10 micron, and worked in the transmission mode.

The resolution of an acoustic microscope is determined by the wavelength $\lambda$ of the sound that is used and by the numerical aperture of the lens or lenses that are used. To achieve a high resolution, it is necessary to work at the highest possible frequency with a large numerical aperture. According to Briggs, p. 45, the best resolution ever obtained with water as the coupling medium is the work of B. Hadiomioglu and C. F. Quate, Appl. Phys. Lett. 43, 1006 (1983). They used sound pulses of frequency 4.4 GHz and 3 ns duration, with a lens of numerical aperture 0.73 and a radius of 15 micron. The resolution in the linear mode was 0.37 micron and with non-linearity was 0.24 micron. Non-linearity refers to the effect that if the amplitude of the sound near to the focus is sufficiently large, higher frequency harmonics are generated. The presence of these shorter wavelength components improves the resolution. Note that 3 ns at 4.4 GHz is only 13 cycles.

When the frequency is increased, the attenuation of the sound in water becomes a severe problem. In water, the attenuation in the GHz frequency range varies as the square of the frequency. At 38° C., human body temperature, the attenuation a per unit distance in water is given by $a=0.016 \, f^2$ micron$^{-1}$, where f is the frequency in GHz. In a reflection microscope, it is necessary to have the time duration t of the acoustic pulse less than the round trip time from the lens surface to the sample and back. When sound is generated by an electrically driven piezoelectric transducer, it is very difficult to make t less than a few ns (say 5 ns), and so the acoustic path length has to be at least 8 micron and preferably somewhat longer. A 5 GHz sound wave would be attenuated by 35 dB after traveling 10 micron. Thus, for a given working distance from the lens to the sample object, the attenuation effectively controls the highest frequency that can be used and consequently limits the resolution. Water is the usual choice for a coupling medium because of its low attenuation. There are liquids with lower attenuation (e.g., He, $H_2$, $CS_2$, Hg, Ga), but there are difficulties in working with these materials. For example, He and $H_2$ cannot be used as coupling liquids at room temperature. For biological samples, water is generally the only possible coupling medium.

Thus, those skilled in the art desire a scanning acoustic microscope with improved resolution. In particular, those skilled in the art desire a scanning acoustic microscope that can use higher frequency pulses of shorter wavelength to improve the resolving power of the scanning acoustic microscope. Further, those skilled in the art desire a scanning acoustic microscope in which the sensor head can be positioned more closely to the sample being imaged to reduce attenuation of the sound waves used for imaging purposes by the coupling medium.

SUMMARY OF THE PREFERRED EMBODIMENTS

A first exemplary embodiment of the invention encompasses an opto-acoustic transducer assembly comprising a substrate; at least one layer of opto-acoustic material coupled to a surface of the substrate, where the at least one layer of opto-acoustic material generates sound waves when struck by light and an acoustic lens to focus sound waves generated by the at least one layer of opto-acoustic material.

A second exemplary embodiment of the present invention comprises a transducer assembly for use in an instrument which is in turn used to probe a sample object, the transducer assembly having dual piezo-electric and opto-acoustic modes of operation, the transducer assembly comprising: a substrate; a layer of opto-acoustic material deposited on a surface of the substrate, the layer of opto-acoustic material being electrically conductive; a layer of piezo-electric material deposited on the layer of opto-acoustic material; a layer of electrically conductive material deposited on the layer of piezo-electric material; an acoustic lens; and where when a pulsed electric potential is applied between the layer of opto-acoustic material and the layer of conductive material, a pulsed electric field is created which causes the layer of piezo-electric material to deform and thereby create pulsed sound waves which are focused by the acoustic lens and then used to probe the sample object, and where after the pulsed sound waves interact with the sample object and are collected by the acoustic lens, the collected pulsed sound waves impinge the layer of opto-acoustic material thereby changing at least one optical property of the layer of opto-acoustic material.

A third exemplary embodiment of the invention includes a scanning acoustic microscope comprising at least one light source for generating pulsed light used at least in a pump mode to generate pulsed sound waves to interact with a sample object to be probed using the pulsed sound waves; and at least one opto-acoustic transducer assembly. The at least one opto-acoustic transducer assembly includes a substrate; at least one layer of opto-acoustic material coupled to a surface of the substrate, where the at least one layer of opto-acoustic material generates pulsed sound waves when struck by the pulsed light generated by the at least one light source; and an acoustic lens to focus pulsed sound waves generated by the at least one layer of opto-acoustic material.

A further exemplary embodiment of the invention comprises a scanning acoustic microscope comprising: a piezo-electric transducer assembly comprising: a substrate; a layer of piezo-electric material formed on a surface of the substrate which generates pulsed sound waves to interact with a sample object to be probed with the pulsed sound waves when a voltage is applied to the layer of piezo-electric material; an acoustic lens formed on or in the substrate to focus the pulsed sound waves; a voltage source coupled to the layer of piezo-electric material; at least one opto-acoustic transducer assembly, where the opto-acoustic transducer assembly is operative to collect pulsed sound waves originally generated by the piezo-electric transducer assembly after the pulsed sound waves have interacted with the sample object, the opto-acoustic transducer assembly comprising: a substrate; a layer of opto-acoustic material formed on a surface of the substrate, where a property of the layer of opto-acoustic material changes when pulsed sound waves collected by the opto-acoustic transducer assembly impinge on the layer of opto-acoustic material; an acoustic lens to collect pulsed sound waves generated by the piezo-electric transducer assembly after the pulsed sound waves have interacted with the sample object; at least one light source for generating pulsed light, where the pulsed light will be used at least in a probe mode to measure the change in a property of the layer of opto-acoustic material caused by the pulsed sound waves collected by the opto-acoustic transducer assembly impinging the layer of opto-acoustic material after the pulsed sound waves have interacted with the sample object; a probe mode optical assembly for coupling the pulsed light generated by the at least one light source to the opto-acoustic transducer assembly; a table for mounting the sample object to be probed; and a computer control for controlling the operation of the scanning acoustic microscope.

Another exemplary embodiment of the invention concerns a method for sensing physical properties of a sample object. The method includes providing an instrument having at least one opto-acoustic transducer assembly; generating first pulsed light waves with a light source; directing the first pulsed light waves to at least one layer of opto-acoustic material incorporated in the at least one opto-acoustic transducer assembly; generating pulsed sound waves through the interaction of the at least one layer of opto-acoustic material and the first pulsed light waves; focusing the pulsed sound waves using an acoustic lens and directing them to the sample object to interact with the sample object in such a way that at least one physical property of the sample object can be sensed through the change brought about by the interaction; collecting the pulsed sound waves with the acoustic lens after the pulsed sound waves have interacted with the sample object; and deriving information concerning the sample object from collected sound waves.

A still further exemplary embodiment of the invention concerns a method for performing a physical operation on a sample object. The method includes providing at least one opto-acoustic transducer assembly; generating pulsed light waves with a light source; directing the pulsed light waves to a layer of opto-acoustic material incorporated in the at least one opto-acoustic transducer assembly; generating pulsed sound waves through the interaction of the layer of opto-acoustic material and the pulsed light waves; focusing the pulsed sound waves using at least one acoustic lens; coupling the pulsed sound waves to a coupling medium, where the focused pulsed sound waves perform a physical operation on the sample object.

In another exemplary embodiment there is provided an opto-acoustic transducer assembly that comprises a substrate having a top surface for receiving pump light and probe light and a bottom surface; a transducer coupled to the bottom surface, said transducer generating sound waves in response to the pump light; and an acoustic lens coupled to said transducer to focus the generated sound waves towards a sample and to collect sound waves returning from the sample. The transducer is comprised of a layer of dielectric material that is interposed between two non-dielectric layers, and where a thickness of the layer of dielectric material is a function of at least a wavelength of the probe light and is modifiable by collected sound waves to cause a detectable change in the probe light.

In one more exemplary embodiment of this invention there is provided an opto-acoustic transducer assembly that comprises a substrate having a top surface for receiving pump light and probe light and a bottom surface; a transducer coupled to the bottom surface, said transducer generating sound waves in response to the pump light; and an acoustic lens coupled to the transducer to focus the generated sound waves towards a sample and to collect sound waves returning from the sample. The transducer is comprised of an optical micro-cavity layer that is interposed between a metal-containing layer and a multi-layered dielectric stack, where a thickness of the optical micro-cavity layer is a function of a wavelength of at least the probe light and is modifiable by collected sound waves to cause a detectable change in the probe light.

In another exemplary embodiment of this invention there is provided an opto-acoustic transducer assembly that comprises a substrate having a top surface for receiving pump light and probe light and a bottom surface; a transducer coupled to the bottom surface, said transducer generating sound waves in response to the pump light; and an acoustic lens coupled to said transducer to focus the generated sound waves towards a sample and to collect sound waves returning from the sample. The transducer is comprised of at least one laterally patterned layer having individual structural features possessing dimensions that are less than the wavelength of light employed.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein:

FIGS. 2A-2B depict cross-sectional and bottom views, respectively, of another opto-acoustic transducer assembly made in accordance with present invention and suitable for use in a scanning acoustic microscope and other instruments;

FIG. 21 shows a first embodiment of a film for detecting a returning sound pulse, the film comprising an array of metal dots surrounded by a dielectric material; and FIG. 22 shows a second embodiment of a film for detecting a returning sound pulse, the film comprising an array of dielectric dots surrounded by a metal.

DETAILED DESCRIPTION OF THE PREFERRED EMBODIMENTS

As employed herein a layer or film may be comprised of single homogenous material, two or more heterogeneous materials, or two or more constituent layers or films (multilayers) comprised of the same or different materials.

It is shown below that the exemplary embodiments of the invention overcome the limitations of the prior art. In the exemplary embodiments of the invention acoustic waves that are used to probe various physical and mechanical properties of samples are generated by the interaction of pulsed light with a material having opto-acoustic properties. Due to the ability to generate ultra-short-width light pulses at a high repetition rate, pulsed sound waves used in embodiments of the present invention have much higher frequencies and much lower wavelengths than in prior art devices. Consequently, in instruments operating in accordance with the present invention, higher frequency sound waves can be used, resulting in a much higher resolution.

In certain embodiments of the present invention acoustic waves used to probe various physical and mechanical properties of samples are generated by the interaction of light waves with a material having opto-acoustic properties. In contrast, known scanning acoustic microscopes use piezoelectric transducers to generate sound. Due to the availability of light sources capable of generating ultra-short-duration light pulses, sound pulses of very short duration can be produced, e.g., pulses with duration below 1 ns, and as short as 0.1 ps. Due to the narrow width of sound pulses in instruments operating in accordance with the present invention, the distance from the sensor element to the sample object can be decreased, thereby reducing the effect of acoustic attenuation experienced on prior art instruments. Consequently, in instruments operating in accordance with the present invention, higher frequency sound waves can be used, resulting in a much higher resolution. In instruments incorporating the improvements of the present invention such as, for example, scanning opto-acoustic microscopes, a frequency of 15 GHz or higher can be used resulting in a lateral resolution for the microscope of 55 nm.

Figure 1:
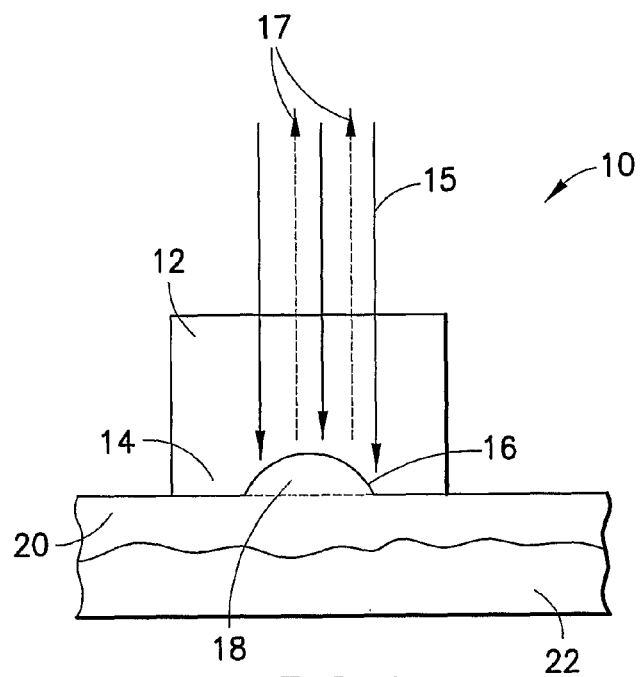
FIG. 1 depicts an opto-acoustic transducer assembly made in accordance with the present invention and suitable for use in a scanning acoustic microscope and other instruments.

An embodiment of the present invention overcoming the limitations of the prior art comprises an opto-acoustic transducer assembly depicted in FIG. 1. The opto-acoustic transducer assembly depicted in FIG. 1 is incorporated in a scanning acoustic microscope performing imaging operations, but one skilled in the art will appreciate that the opto-acoustic transducer assembly of the present invention can be used in other instruments to probe other physical and mechanical properties of a sample object.

The opto-acoustic assembly 10 depicted in FIG. 1 comprises a substrate 12 in which a thin film 14 of a material having opto-acoustic properties is deposited onto a surface of a concave semi-hemispherical cavity 16. The cavity, which operates as an acoustic lens 18, can be formed by various methods known to those skilled in the art, for example in a polymeric material by using a silica sphere as a mold and etching out the silica sphere. Alternatively, the hemispherical acoustic lens 18, approximately 0.5 um in radius, can be fabricated into sapphire (or comparable material) by electron beam grey scale lithography and dry etching. Amorphous $As_2Se_3$ is a compatible material which can be vacuum-deposited as the thin film transducer with high optical absorption at the pump laser wavelength, but this material is mentioned only as an example, since there are other suitable materials.

In order so that the opto-acoustic transducer 10 assembly need not contact the sample object 22 the angle defined by the surface of the concave semi-hemispherical cavity 16 in cross section is less than 180°. This is the reason the cavity is referred to as "semi-hemispherical."

In an alternative implementation to that depicted in FIG. 1, an optically transparent pinhole (having a diameter less than 100 nm for example) is incorporated in the assembly to accommodate a near field optical imaging instrument, thereby providing dual, optical and acoustical imaging modes for the device.

In the opto-acoustic transducer assembly 10 depicted in FIG. 1, ultra-short-duration laser pulses 15 (for example, at a duration of $10^{-13}$ s) at a rapid repetition rate provide both the excitation input and the imaging input to the microscope via a thin film transducer 14 which is integrated into a focusing/imaging objective to convert optical energy to ultrasound and vice/versa. After travel through a sapphire substrate or equivalent 12, a "pump" laser pulse is absorbed in the transducer 14, causing an ultrashort transient stress. As the thickness of the transducer undergoes a sudden change, an acoustic pulse is launched into the coupling fluid 20 (for example, water). The acoustic pulse propagates and is focused by the acoustic lens 18 and interacts with a sample object 22 in a reflective mode, although other modes such as, for example, transmitting modes can be used in embodiments of the present invention. Upon return, changes in the optical constants of the thin film 14 are detected by a time-delayed probe laser pulse 17 shown after reflection off of the thin film 14.

In embodiments operating in a transmitting mode, two opto-acoustic transducer assemblies are employed. The first opto-acoustic transducer assembly generates sound waves to interact with the sample object, and the second opto-acoustic transducer assembly collects and detects sound waves after the sound waves have interacted with the sample object.

A particular advantage of optical generation of acoustic waves is that in instruments operating in accordance with the present invention, the acoustic path can be reduced to 1 micron or less, thereby decreasing the attenuation of the sound waves caused by the coupling medium. Other advantages of the present invention result from the reduction in the acoustic path—namely the ability to use a considerably higher acoustic frequency and thereby achieve a higher resolution than heretofore known in such instruments. In a scanning acoustic microscope operating in accordance with the present invention having the ability to precisely control the movement of the opto-acoustic transducer assembly 10, a 10-100 GHz ultrasound image will be acquired, mirroring local variations in acoustic material density at a nanoscale level.

As just noted, the acoustic path is short compared to the path between the transducer and the sample object for a conventional acoustic microscope. However, it is important to note that the distance of the transducer from the sample object can be kept large enough to make the risk of the transducer making mechanical contact with the sample object very small. Accidental mechanical contact with the sample object is a significant problem with other microscopy methods of comparable resolution, (e.g. near field scanning optical microscopy and atomic force microscopy) because in these methods the distance of the scanning probe is less than 100 nm.

FIGS. 2A-B are cross-sectional and bottom views, respectively, depicting another embodiment of an opto-acoustic transducer assembly 40 operating in accordance with the present invention. The embodiment 40 depicted in FIG. 2 operates as an acoustic analogue to a Fresnel lens. In the embodiment depicted in FIG. 2, a plurality of non-contiguous rings of opto-acoustic material is deposited on a surface 44 of a substrate 46 and comprises a transducer and acoustic lens 42. Pump mode light pulses 45 are shown impinging on the transducer 42. Pulsed sound waves 47 are created by the interaction of the pump mode light pulses and opto-acoustic material. The pulsed sound waves 47 are then coupled to a coupling medium 48 and strike the sample object 50. The structure of the transducer and acoustic lens 42 operates on the principle of ultrasound wave diffraction. The alternate zones of the transducer and acoustic lens 42 are adjusted to have much different optical absorption so that the launch of the ultra-short strain pulses follows the zone plate's spatial geometry (a burst of ultra-short-duration pulses is used in the Fresnel-lens-like embodiment so that the acoustic energy can be concentrated to a sharp focus by successive pulses arriving from different zones). The Fresnel-lens-like construction of the opto-acoustic transducer assembly 40 depicted in FIG. 2 has the advantage of being compatible with both crystalline and amorphous multi-layer materials and with microelectronic planar patterning and processing techniques. In one possible embodiment, the thin layer comprising the Fresnel-lens-like transducer 42 is formed by successively depositing layers of GaN, InGaN and Cr on a sapphire substrate. Embodiments constructed in this manner exploit the very large piezo effects in the GaN-based heterostructure system where interband optical absorption has been shown to offer means of generating intense high-frequency acoustic phonons.

In another embodiment of the Fresnel-lens-like optical transducer, each layer, of the transducer 42 vibrates at a chosen frequency (e.g., 15 GHz) for several cycles (e.g., 2-10) after it is excited by a single pump pulse. The number of cycles that the transducer vibrates is determined by the difference between the acoustic impedance Zf of the transducer material and the acoustic impedance Zs of the substrate. (Acoustic impedance is the product of the mass density and the sound velocity.) If Zf is much less than Zs or if Zf is much greater than Zs, then after the transducer film is excited by the pump light pulse the film will vibrate for several cycles before its oscillation is damped out. In this way it is possible to excite the Fresnel-lens-like optical transducer with a single pump light pulse and still produce constructive interference of the acoustic waves from the different zones at the acoustic focus.

In another embodiment of the Fresnel-lens-like optical transducer assembly 40 depicted in FIG. 2, the central zone 52 is maintained as being transparent. The maintenance of the transparency of the central zone 52 provides a sub-wavelength optical aperture for use by a near-field optical microscope in a scanning microscope having both acoustic and optical modes of operation.

Figure 3:
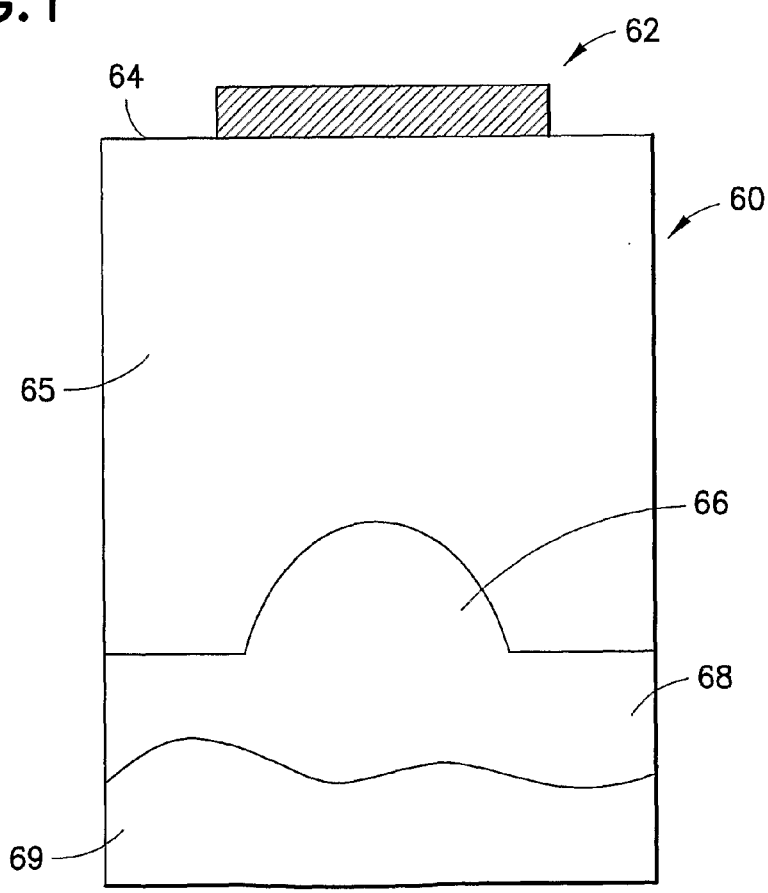
FIG. 3 depicts a further opto-acoustic transducer assembly made in accordance with the present invention and suitable for use in a scanning acoustic microscope and other instruments.

A further embodiment of the opto-acoustic transducer assembly 60 of the present invention is depicted in FIG. 3. In the embodiment depicted in FIG. 3, a planar layer 62 of opto-acoustic material is deposited on a surface 64 of a substrate 65. When light pulses strike the planar layer 62 of opto-acoustic material sound waves are generated and propagate to a semi-hemispherical acoustic lens 66 formed in the substrate 65, where they are focused. The sound waves are then coupled to a coupling fluid 68, after which they interact with a sample object 70.

The opto-acoustic transducers depicted in FIGS. 1-3 above are designed to generate sound waves that are focused into a small volume with linear dimensions of the same order of magnitude as the wavelength of the sound. If the acoustic wavelength is very small, the sound is focused to a region close to a point, and consequently this is referred to as point focusing. "Point focusing" as described herein refers to what may be accomplished with practical apparatus.

It is also possible to use an opto-acoustical transducer that focuses sound into a region that is close to a line (line focusing) and this may be advantageous for the study of certain types of sample objects. There are a number of ways of achieving line focusing. One method is to use an opto-acoustic transducer in which the sound generated by the layer of opto-acoustic material is focused by a cylindrical surface as depicted in FIG. 4.

Figure 4:
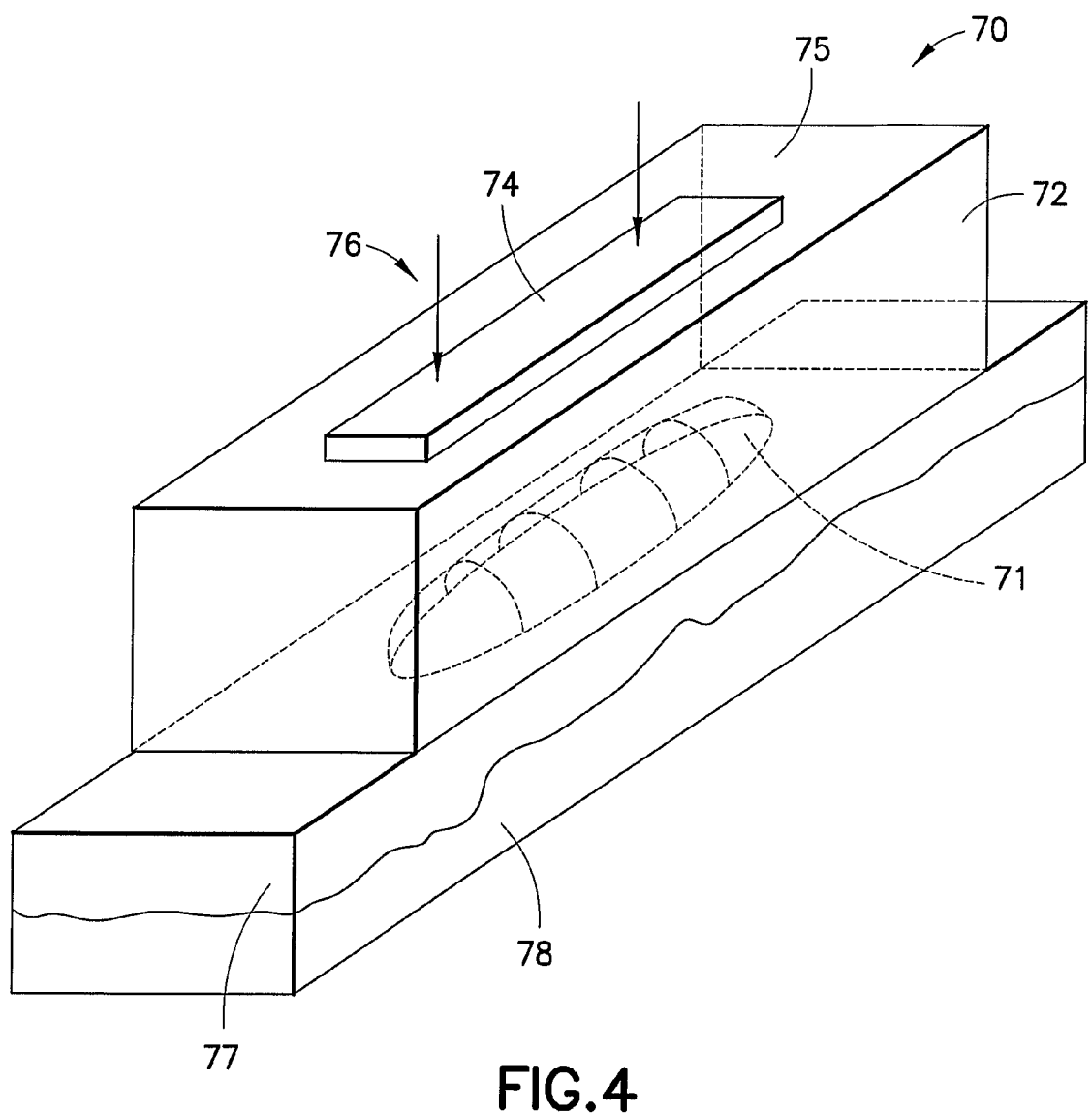
FIG. 4 depicts yet another opto-acoustic transducer assembly made in accordance with the present invention and suitable for use in a scanning acoustic microscope and other instruments.

In the opto-acoustic transducer assembly 70 depicted in FIG. 4, a semi-cylindrical cavity 71 is formed in a substrate 72. "Semi-cylindrical" refers to the fact that an angle subtended by the semi-cylindrical surface is less than 180° so that the substrate 72 need not contact the sample 78. A layer of opto-acoustic material 74 is deposited on a surface 75 of the substrate. Pump mode light pulses 76 strike the layer of opto-acoustic material 74 and create pulsed sound waves. The pulsed sound waves propagate through the substrate 72 and are focused by the semi-cylindrical cavity 71. The sound waves are then coupled to the coupling medium 77 after which they strike the sample object 78.

Figure 5:
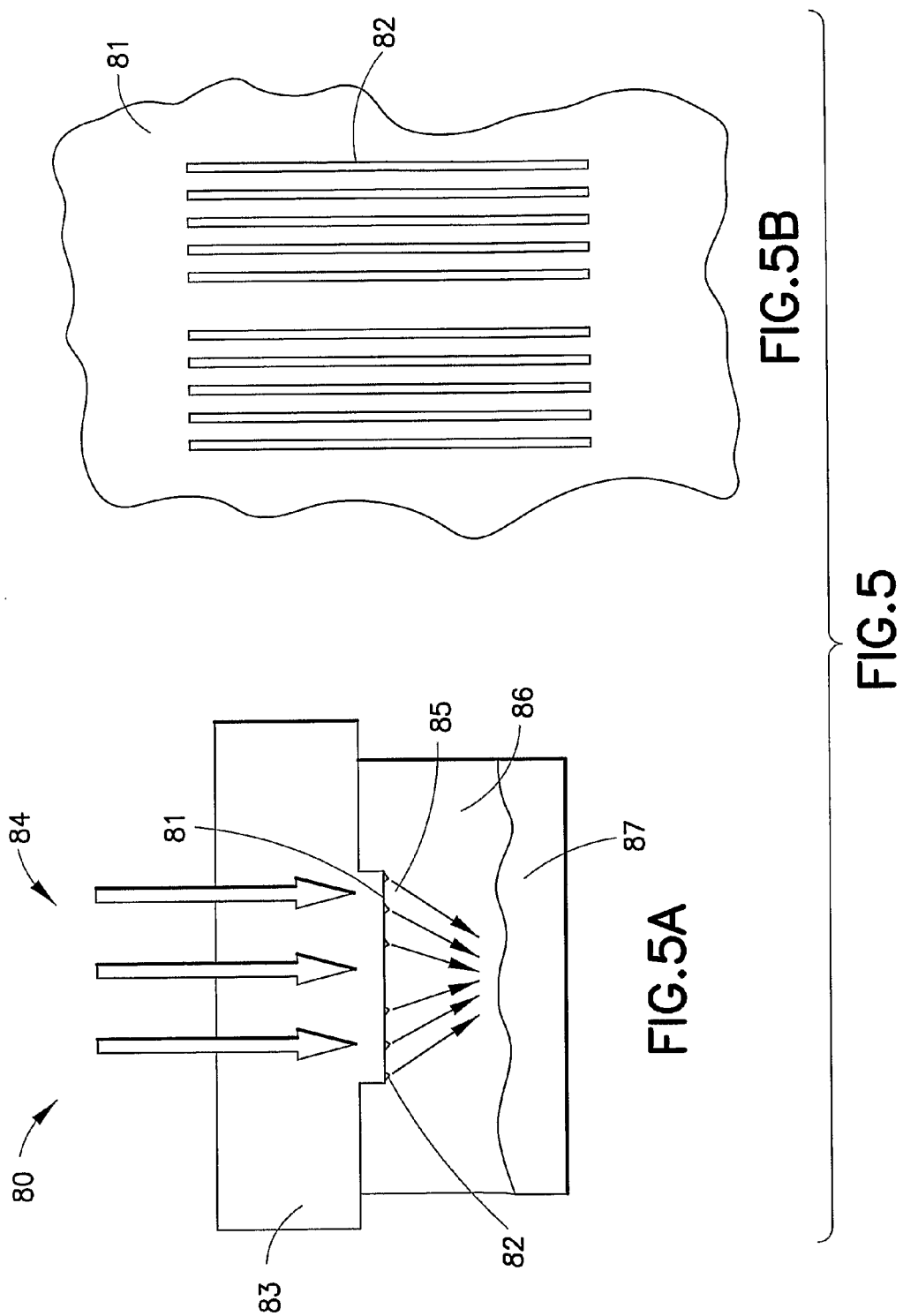
FIGS. 5A-5B depict cross-sectional and bottom views, respectively, of a still further opto-acoustic transducer assembly made in accordance with the present invention and suitable for use in a scanning acoustic microscope and other instruments.

In another embodiment capable of line focusing a structure analogous to the Fresnel-lens-like structure already described is used as depicted in FIGS. 5A-5B. The opto-acoustic transducer assembly 80 of this embodiment is shown in cross-section in FIG. 5A and from the bottom in FIG. 5B. The transducer and acoustic lens 81 comprises a plurality of parallel non-contiguous strips of opto-acoustic material deposited onto a planar surface 82 of a substrate 83. As in the case of the other embodiments, pump mode pulsed light waves 84 impinge the transducer and acoustic lens 81. The spacing and width of the strips of opto-acoustic material comprising the transducer and acoustic lens 81 are chosen so that the launch of the ultra-short strain pulses caused by the impinging probe mode light pulses 84 results in acoustic energy being concentrated to a line focus by successive pulses arriving from different strips. The focused sound pulses are then coupled to coupling medium 87 and strike sample object 87.

Figure 6:
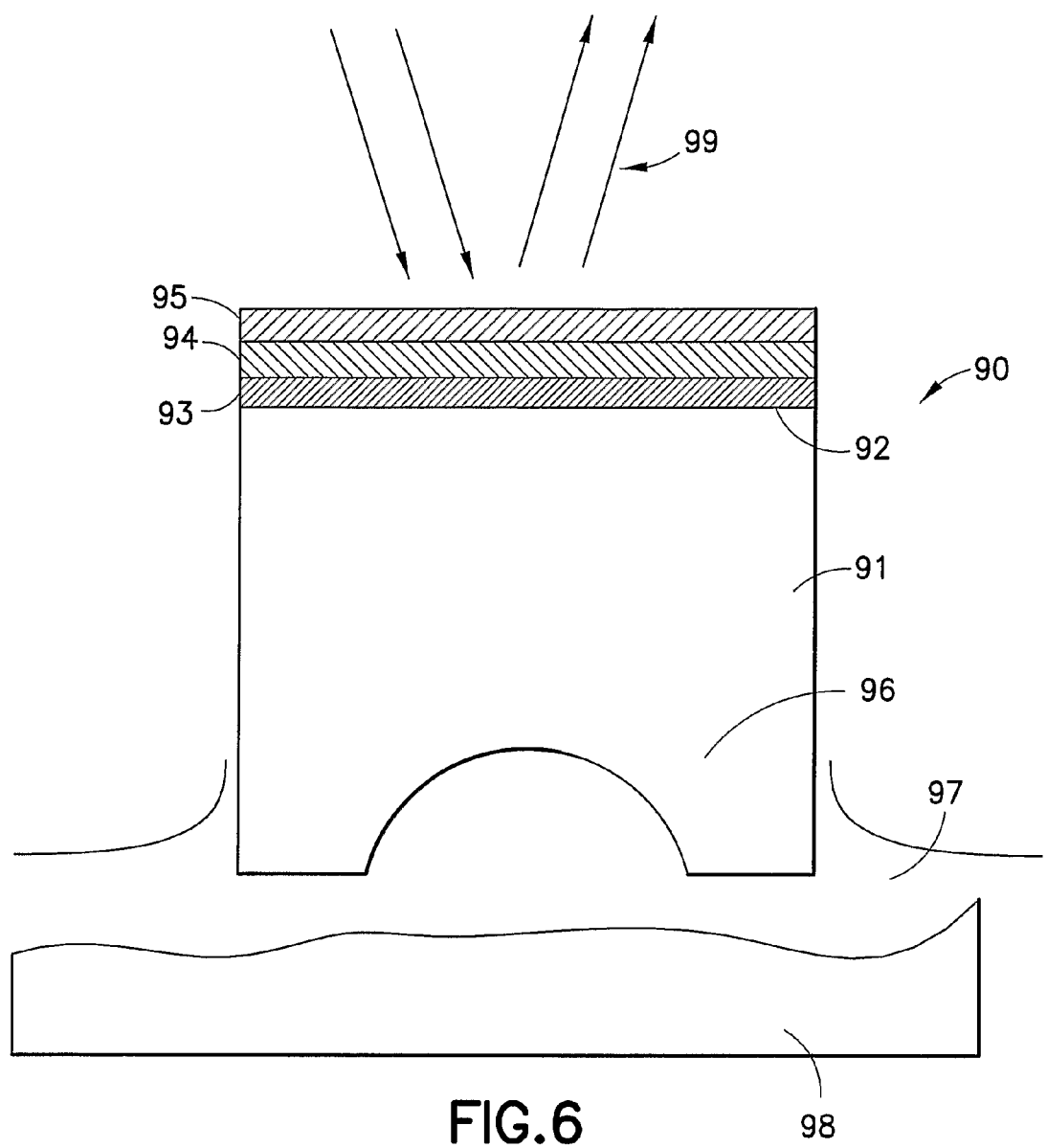
FIG. 6 depicts a transducer assembly having dual piezoelectric and opto-acoustic modes of operation made in accordance with the present invention and suitable for use in a scanning acoustic microscope.

Another embodiment of a transducer assembly suitable for use in a scanning acoustic microscope and operating in a dual piezo-electric and opto-acoustic mode is depicted in FIG. 6. In this particular embodiment, the dual-mode transducer 90 includes a substrate 91 of material with low acoustic attenuation, such as sapphire. On an upper planar surface 92 of the substrate are deposited in sequence a film 93 of $As_2Te_3$, a film 94 of piezoelectric material such as zinc oxide, and a film 95 of indium tin oxide (ITO). ITO and $As_2Te_3$ are conducting materials. Consequently by making electrical connections to films 93, 95 and applying a voltage to these connections, an electric field is produced across the piezoelectric film 94. By applying the voltage as a short pulse it is possible to generate a sound pulse. This sound pulse travels down the substrate 91, across the spherically-curved surface 96 at the bottom of the substrate and then comes to a focus in the coupling fluid 97. After interacting with the sample 98, the returning sound passes through the coupling fluid and travels up through the substrate to the $As_2Te_3$ film. Through the piezo-optic effect the sound changes the optical properties of this film. These changes are sensed through the application of an ultrashort light pulse 99. Note that although the ITO film is an electrical conductor, it is transparent to light and thus the ultrashort light pulse is able to pass through it so as to sense the optical properties of the $As_2Te_3$ film. Other materials can be used for the detection film in place of $As_2Te_3$, and other piezoelectric materials can be used in place of zinc oxide for the generation film. In the embodiment of the present invention shown in FIG. 6, a piezoelectric transducer is used to generate sound and a light pulse is used to detect sound. It is also within the scope of the invention to generate sound using a light pulse and then detect sound with a piezoelectric transducer. It is also possible to use other types of acoustic transducers, e.g., magnetic transducers, in place of the piezoelectric film.

Figure 7:
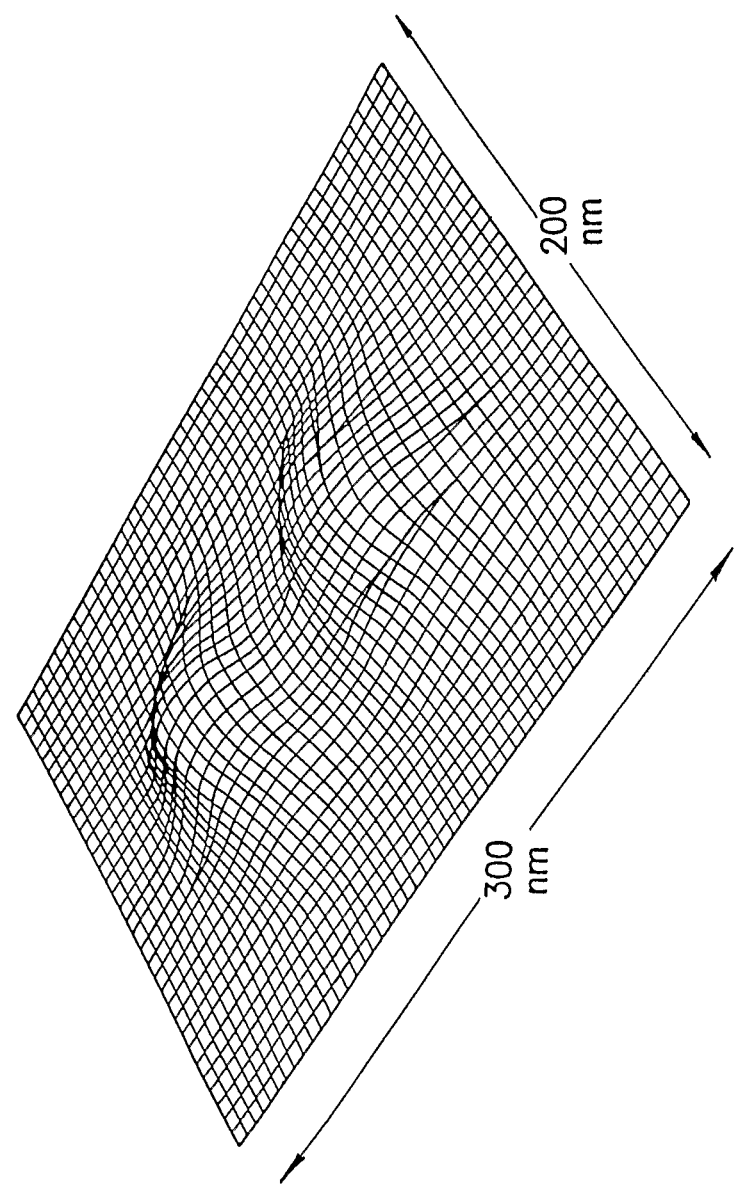
FIG. 7 is a graph depicting the results of a simulation showing the resolution of an opto-acoustic transducer assembly operating in accordance with the present invention.

The resolving power of various embodiments of the opto-acoustic transducer assembly of the present invention has been estimated. For example, consider the Fresnel-lens-like embodiment depicted in FIG. 2. The acoustic lens consists of five elements with the center ring having an inner diameter of 400 nm and outer ring with outer diameter of 1600 nm. The distance from the center of the lens to the focus is 400 nm and the lens is designed for operation at 15 GHz. The sound field coming from the lens is calculated using Huygens' Principle including the directional factor. The transducer is taken to be excited by a sequence of five light pulses at intervals of 67 ps, that is, $(15\ \text{GHz})^{-1}$. In the simulation, the attenuation of the different Fourier components of the sound field is accounted for. The object is two point reflectors located in the plane at 400 nm below the lens and separated by a distance d. FIG. 7 shows a plot of the returning acoustic field integrated over the active area of the Fresnel lens as a function of the position of the lens relative to the object. The separation d between the two point reflectors in FIG. 7 is 100 nm. The simulations indicate that the lateral resolution of the microscope operating at 15 GHz is approximately 50 nm; this is based on the Sparrow criterion.

The vertical resolution depends on the signal-to-noise ratio of the overall system. For an object whose height varies smoothly with lateral position, height changes of a small fraction of the acoustic wavelength λ, i.e., 0.1 to 10 nm can be resolved. The attenuation in water decreases monotonically with increasing temperature in the range 0 to 100° C.; the attenuation at 20° C. is 2.5 times the attenuation at 60° C. Thus the highest frequency that can be used decreases as the temperature goes down, and the resolution is lower.

For work with non-biological samples at room temperature (20° C.) fluids with attenuation lower than water may be used. At low frequencies where $\omega\tau<1$ (ω is the angular frequency of the sound, and τ is the structural relaxation time), the attenuation varies as $\omega^2\tau$. However, if τ becomes so long that $\omega\tau>1$, the attenuation varies as $\tau^{-1}$ and is independent of ω. In a glass-forming liquids τ becomes very large as the temperature is reduced towards the glass transition temperature and the attenuation (e.g., for >15 GHz) drops dramatically while the viscosity is still low enough for the liquid to be useful as a coupling fluid.

In the various embodiments depicted in FIGS. 1-5, a pump pulse of duration between 0.1 and 1000 ps is used to excite the transducer films of opto-acoustic material. The energy deposited in the transducer films by the pump pulse causes it to expand and this expansion launches a sound pulse into the water coupling medium. The sound travels to the acoustic focus and then returns to the transducer film in a reflective implementation. In a transmitting embodiment the sound waves continue to a second opto-acoustic transducer assembly. In either situation, when the sound waves enter the transducer film they cause a change in the optical properties of the film. This change is sensed by means of a time-delayed probe optical pulse. In the currently preferred embodiment, the pump and probe pulses come from the same pulsed laser source such as the Coherent Chameleon XR compact ultrafast laser. It is likely that in the next few years much less expensive lasers with similar performance will become commercially available. The delay of the probe pulse with respect to the pump is determined by changing the optical path for the probe pulse through the use of a retro-reflector mirror mounted on a computer-controlled translation stage, as will be shown in the following description of scanning acoustic microscopes incorporating opto-acoustic transducer assemblies of the present invention.

Different methods can be used to generate an acoustic pulse with a characteristic frequency. In the case of the opto-acoustic transducer assembly having a concave acoustic lens as depicted in FIGS. 1, 3 and 4, it is possible to select a material and thickness for the thin film such that when excited by a single light pulse the film vibrates with the desired frequency. These vibrations will damp out in a certain time that is governed by the rate at which acoustic energy is transferred into the water coupling medium and into the substrate upon which the film is deposited. If the acoustic impedance of the film is small compared with the acoustic impedance of the substrate material upon which it is deposited, the film will form a so-called resonator. The frequency of vibration will be determined by the sound velocity in the film and the thickness. It may also be advantageous to use a film composed of multiple layers to obtain the desired frequency and at the same time achieve a good coupling of the sound from the film structure into the water. For the Fresnel-lens-like embodiment depicted in FIGS. 2A-2B, the transducer is excited by a series of light pulses (e.g., 2-10) so that the sound launched from each ring of the transducer arrives at the acoustic focus at the same time. Alternatively, a single pump light pulse can be used together with a transducer film that vibrates for several cycles after excitation as already described.

Figure 8:
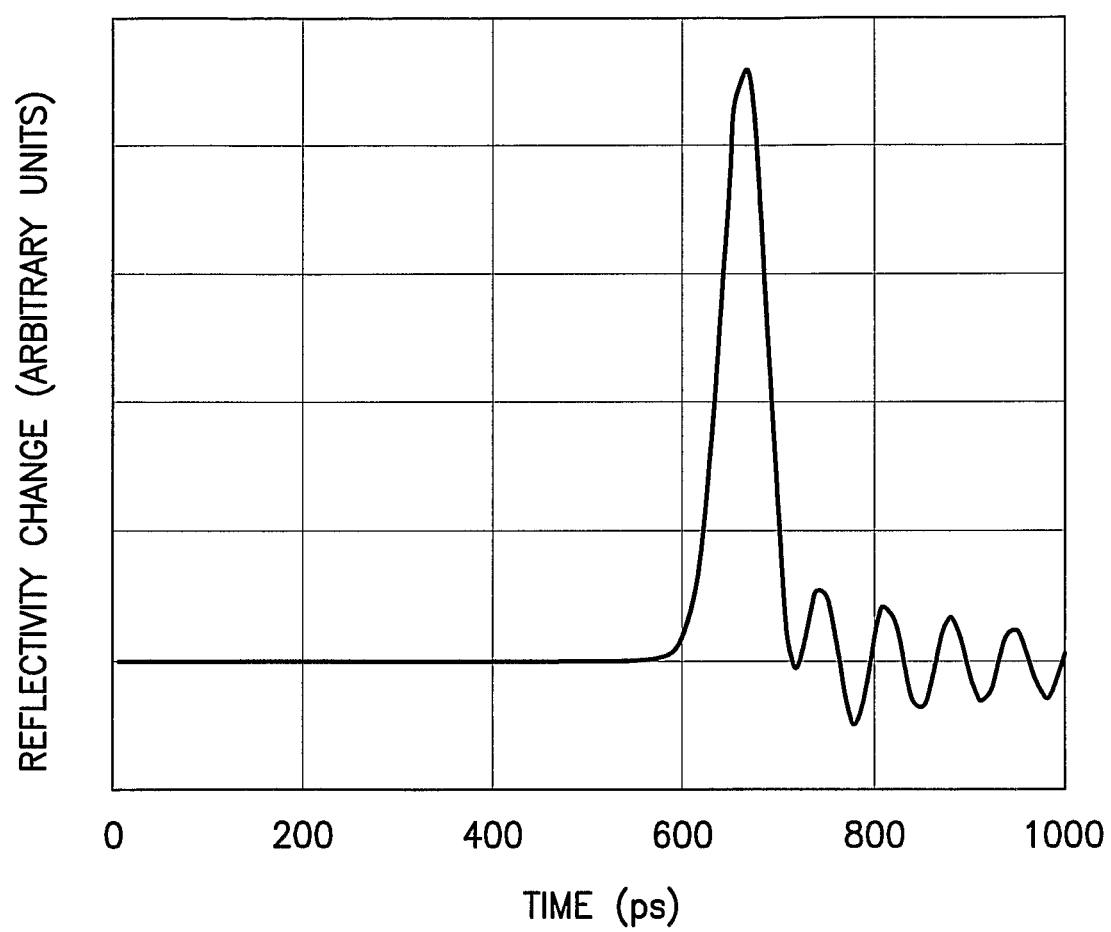
FIG. 8 is a graph depicting the results of a simulation showing the change in the reflectivity of a probe light pulse as a function of the time at which it is incident upon a transducer operating in accordance with the present invention.

For any of the embodiments depicted in FIGS. 1-5, the time at which the probe pulse is applied can be selected so as to obtain the most useful information. FIG. 8 shows the results of a simulation of the change in reflection of the probe light pulse as a function of the time of application of the probe pulse. This simulation is for an embodiment similar to that depicted in FIG. 1 with a lens radius of 500 nm, semi-angle 80°, with a transducer film that vibrates at 15 GHz with a damping time of 300 ps. It can be seen that if the probe light pulse is applied at a time of 650 ps after the exciting pump pulse the signal will be a maximum. It may be preferable, however, to apply the probe pulse at a time such as 670 ps where the signal is varying rapidly with the time of application of the probe. If the probe pulse is applied at such a time, there will be a large change in the signal if the distance of the sample object from the lens changes.

To appreciate the advantage of this selection of the probe time, consider the application of the invention to the study of the surface topography of a sample, such as the surface of a planar optical element, e.g., an optical flat. The acoustic lens is moved laterally above the surface of the sample so that the acoustic focus is directed to different points on the surface. If a point on the surface of the nominally planar object is higher than the surrounding area, the acoustic pulse will return to the acoustic lens in less time when the acoustic focus is at this point. Hence, with the probe time set at 670 ps, this high point of the sample will give a decreased signal. For a point that is lower, the signal will be increased. Thus, the signal gives a measure of the height of the surface at the acoustic focus, and by measuring the signal while the acoustic lens is scanned across the surface it is possible to make a topographic map of the surface of the sample object. In an alternative procedure, the acoustic lens can be scanned laterally across the surface of the sample while the height of the lens is adjusted at each point so as to keep the signal at a constant level. The height of the lens is recorded as a function of the lateral position of the lens. A plot of the height of the lens as a function of lateral position gives a topographic map of the surface of the sample object.

Figure 9:
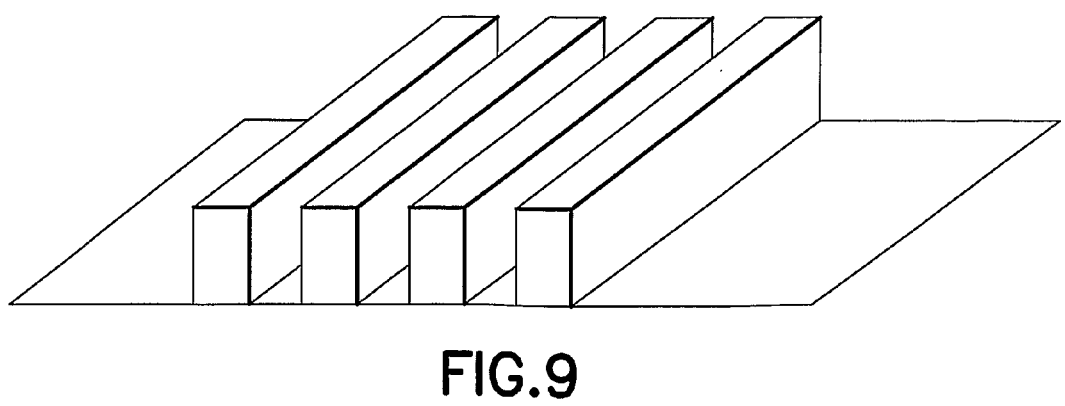
FIG. 9 depicts a line structure in a semiconductor device the properties of which can be probed with the apparatus and methods of the present invention.

The invention is well suited to the measurement of the topography of surfaces onto which have been placed high-aspect ratio structures. For example, in the semiconductor industry, thin films are etched to produce line or dot geometries as shown, for example, in FIG. 9. The spacing between these lines (see FIG. 9) may be as small as 50 nm, while the height may be several times the spacing. The geometry of such structures cannot be measured by optical microscopy because the light has too large a wavelength to penetrate to the bottom of the trenches between the lines. The very short acoustic wavelength of the sound pulses used in the present invention makes it possible for the sound to reach the bottom of the trenches and as a result the geometry of the structure can be measured.

While water has been the preferred coupling medium for most acoustic microscopes, it is possible that other liquids may be found to have more desirable properties for use in the current invention. Conventional acoustic microscopes have operated in the frequency range up to a few GHz, and in this frequency range water has a lower attenuation than other liquids that could be used (see above). However, in the new invention a higher acoustic frequency (10 GHz or higher) will be used and in this higher frequency range other liquids may have a lower attenuation.

Figure 10:
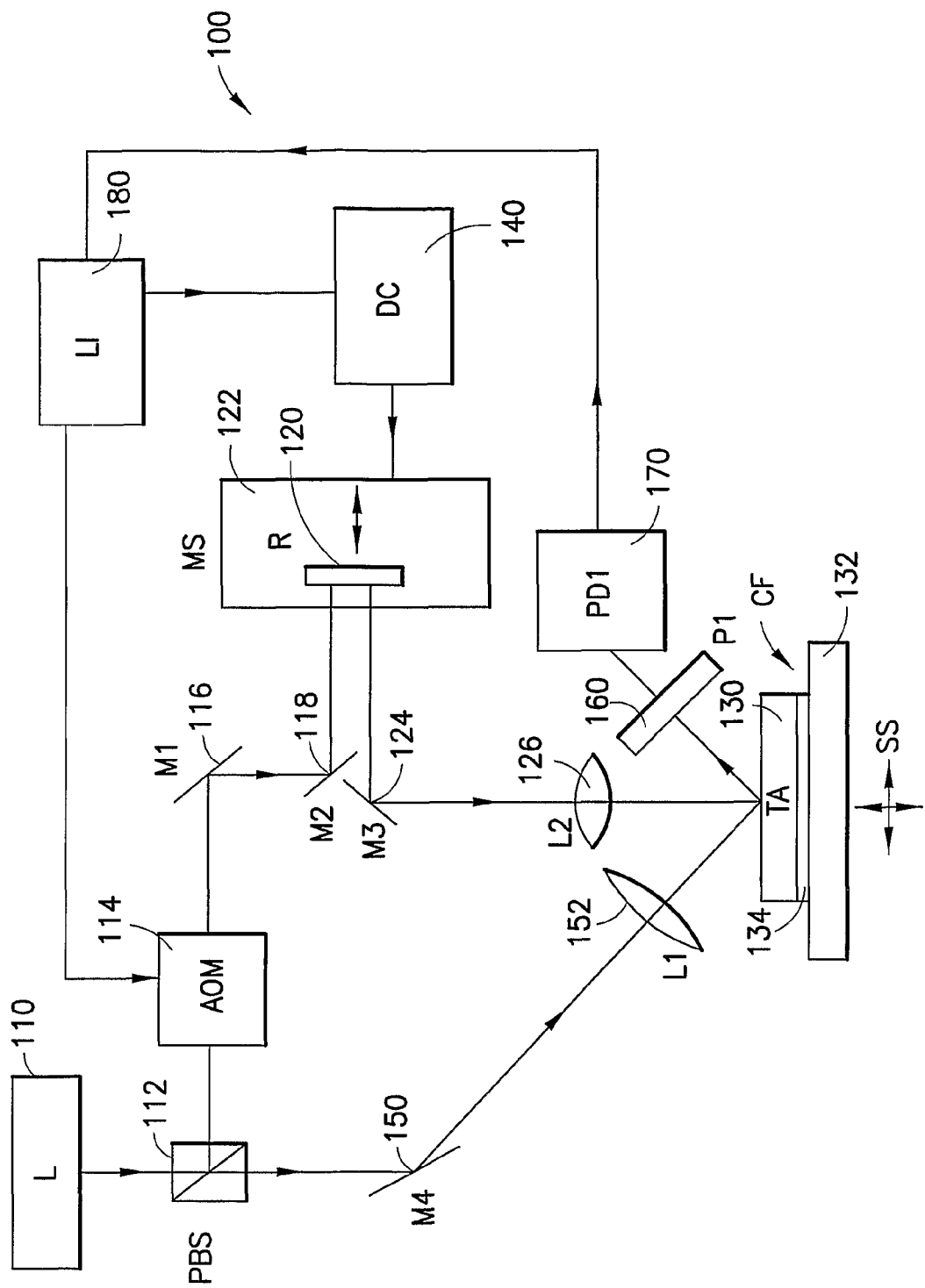
FIG. 10 is a schematic block diagram depicting a scanning acoustic microscope having an opto-acoustic transducer assembly, all made in accordance with the present invention.

The next portion of the disclosure will describe various embodiments of scanning acoustic microscopes incorporating opto-acoustic transducer assemblies, all made in accordance with various embodiments of the present invention. FIG. 10 depicts in schematic form a scanning acoustic microscope 100 of the present invention. A pulsed laser 110 generates a series of short light pulses. Each pulse is split into two by means of a polarizing beam splitter ("PBS") 112. One component, "the pump pulse", is directed into an acousto-optical modulator ("AOM") 114, and then by mirrors 116, 118 to a reflector 120 mounted on a computer-controlled movable stage 122. Mirror 124 then directs the pulse to lens 126 which couples the light to the substrate of the opto-acoustic transducer assembly 130. The movable stage MS 122 is under the control of the digital computer DC 140, and is used to control the arrival time of the pump pulses at the transducer assembly TA 130.

The other component of the laser pulse coming from the polarizing beam splitter 112 is referred to as the "probe pulse." Each probe pulse is directed by mirror M4 150 to lens L1 152 which focuses the light onto the opto-acoustic transducer assembly 130. After reflection by the layer of opto-acoustic material of the opto-acoustic transducer assembly, the probe pulses pass through the polarizer P1 160 and are then detected by the optical detector PD 1170. The polarizer 160 is oriented so as to block scattered pump light from reaching the detector. The output of this detector 170 is fed into the signal input of the lock-in amplifier L1 100. The demodulated output from the lock-in amplifier 180 is directed to the digital computer DC 140 for analysis. The reference output from lock-in amplifier L1 180 is used to drive the acousto-optical modulator AOM 114.

A sample is placed on a sample stage 132, and is coupled to the opto-acoustic transducer assembly 130 by a coupling fluid 134.

Examples of pulsed lasers suitable for use in the measuring system include an Argon ion-pumped Ti:sapphire laser such as the Inova/Mira system manufactured by Coherent, YAG lasers, and the Chameleon diode pumped Ti:sapphire laser manufactured by Coherent. These lasers generate light pulses with a repetition rate $f_1$ in the range 50 to 100 MHz, but lasers with pulse rates outside this range can also be used as a light source for this invention. A currently preferred, but non-limiting, frequency of operation $f_2$ for the acousto-optic modulator is 1 MHz. However, it may be preferable to use a different frequency in the range 1 kHz to 100 MHz according to the noise characteristics of the laser source that is used.

Each pump light pulse sets up a stress in the layer of opto-acoustic material incorporated in the opto-acoustic transducer assembly 130 that launches a sound pulse into the coupling fluid CF 134. After this sound pulse is reflected from the sample, it returns to the transducer 130 and causes a small change in the optical reflectivity of the opto-acoustic material incorporated in the opto-acoustic transducer assembly 130. The probe light pulse is used to measure this small change. The acousto-optic modulator AOM 114 varies the amplitude of the pump pulses at frequency $f_2$ and, as a consequence, the reflectivity of the sample is modulated by a small amount at this same frequency. This results in a modulation of the intensity of the reflected light. The voltage output of the detector PD1 170 is directed to the lock-in amplifier L1 180 which detects the amplitude and phase of the output voltage.

In the presently preferred embodiments, the measured quantity is the change in the intensity of the reflected probe light. It is also within the scope of the invention to measure the change in other characteristics of the probe light after it has been reflected from the opto-acoustic material. These characteristics include, but are not limited to, the phase of the reflected light, the direction of the reflected light, and the polarization of the reflected light. It is also possible to measure the change in the intensity, or other characteristics, of the transmitted probe light.

The sample stage SS 132 provides positioning control of the sample in three dimensions. Let z be the axis perpendicular to the axis of the ultrasonic transducer and x and y axes perpendicular to z. Translating the sample in the z direction can be used to position the plane of the sample relative to the acoustic focus, and translation in x and y is used to make an ultrasonic image of the surface of the sample.

It is within the scope of the invention to use an electro-optic modulator in place of the acousto-optic modulator AOM 114.

Figure 11:
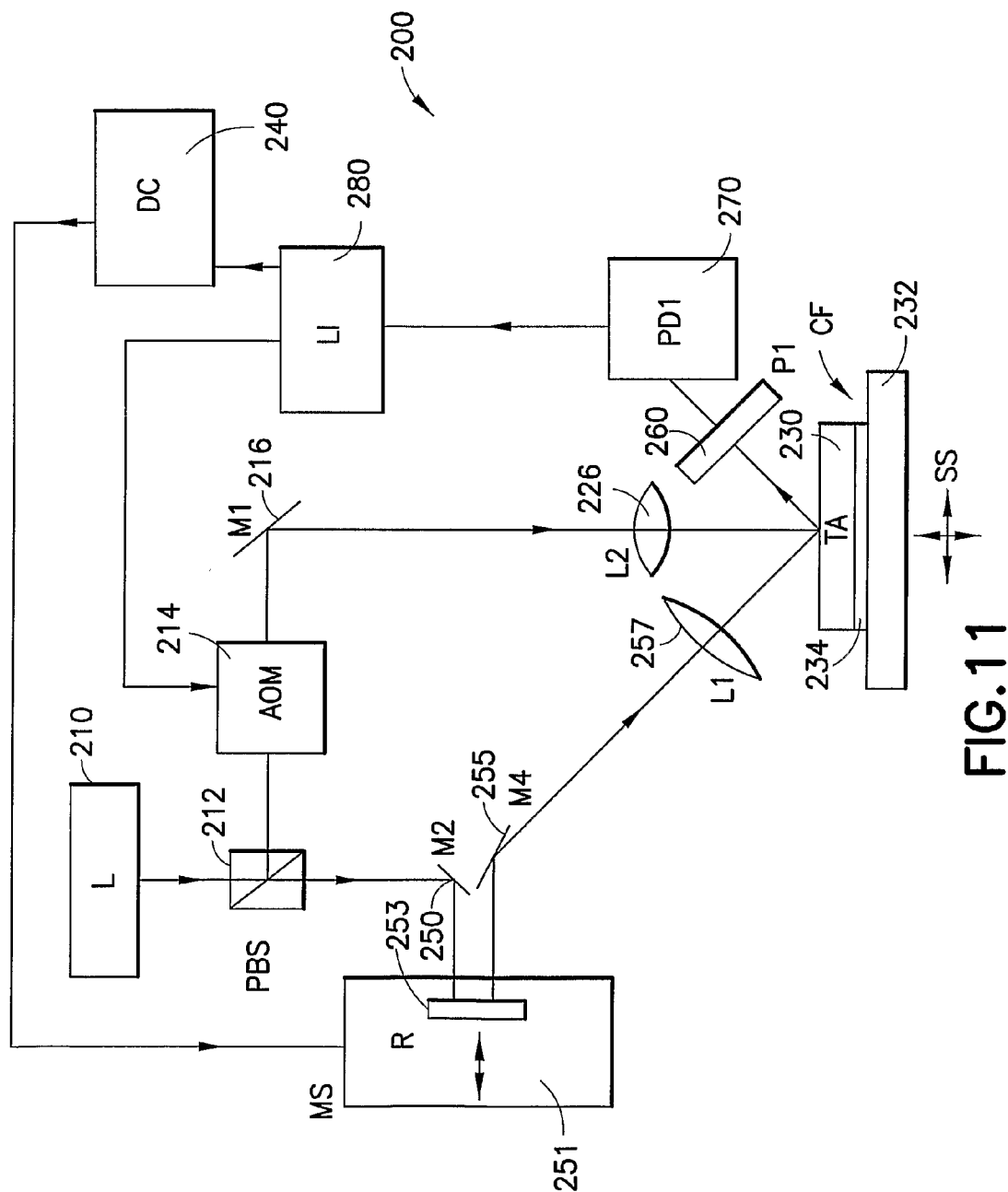
FIG. 11 is a schematic block diagram depicting another scanning acoustic microscope having an opto-acoustic transducer assembly, all made in accordance with the present invention.

FIG. 11 shows an alternative embodiment 200 in which the adjustable time-delay provided by the movable stage is applied to the probe pulses instead of to the pump pulses. In the embodiment depicted in FIG. 11, a pulsed laser 210 generates a series of short light pulses. Each pulse is split into two by means of a polarizing beam splitter ("PBS") 212. The pump pulse is directed into acousto-optical modulator ("AOM") 214, and then by mirror 216 to lens 226 which couples the light to the substrate of the opto-acoustic transducer assembly 230.

In the embodiment depicted in FIG. 11, the probe pulse is directed by mirror 250 to the reflector 253 mounted on movable stage 251. Each probe pulse is then directed by mirror 255 to lens L1 252 which focuses the light onto the opto-acoustic transducer assembly 230. The movable stage MS 251 is under the control of the digital computer DC 240, and is used to control the arrival time of the probe pulses at the transducer assembly TA 230.

After reflection by the layer of opto-acoustic material of the opto-acoustic transducer assembly 230, the probe pulses pass through the polarizer P1 260 and are then detected by the optical detector PD1 270. The polarizer 260 is oriented so as to block scattered pump light from reaching the detector 270. The output of this detector 270 is fed into the signal input of the lock-in amplifier L1 280. The demodulated output from the lock-in amplifier 280 is directed to the digital computer DC 240 for analysis. The reference output from lock-in amplifier L1 280 is used to drive the acousto-optical modulator AOM 214.

A sample is placed on a sample stage 232, and is coupled to the opto-acoustic transducer assembly 230 by a coupling fluid 234.

Figure 12:
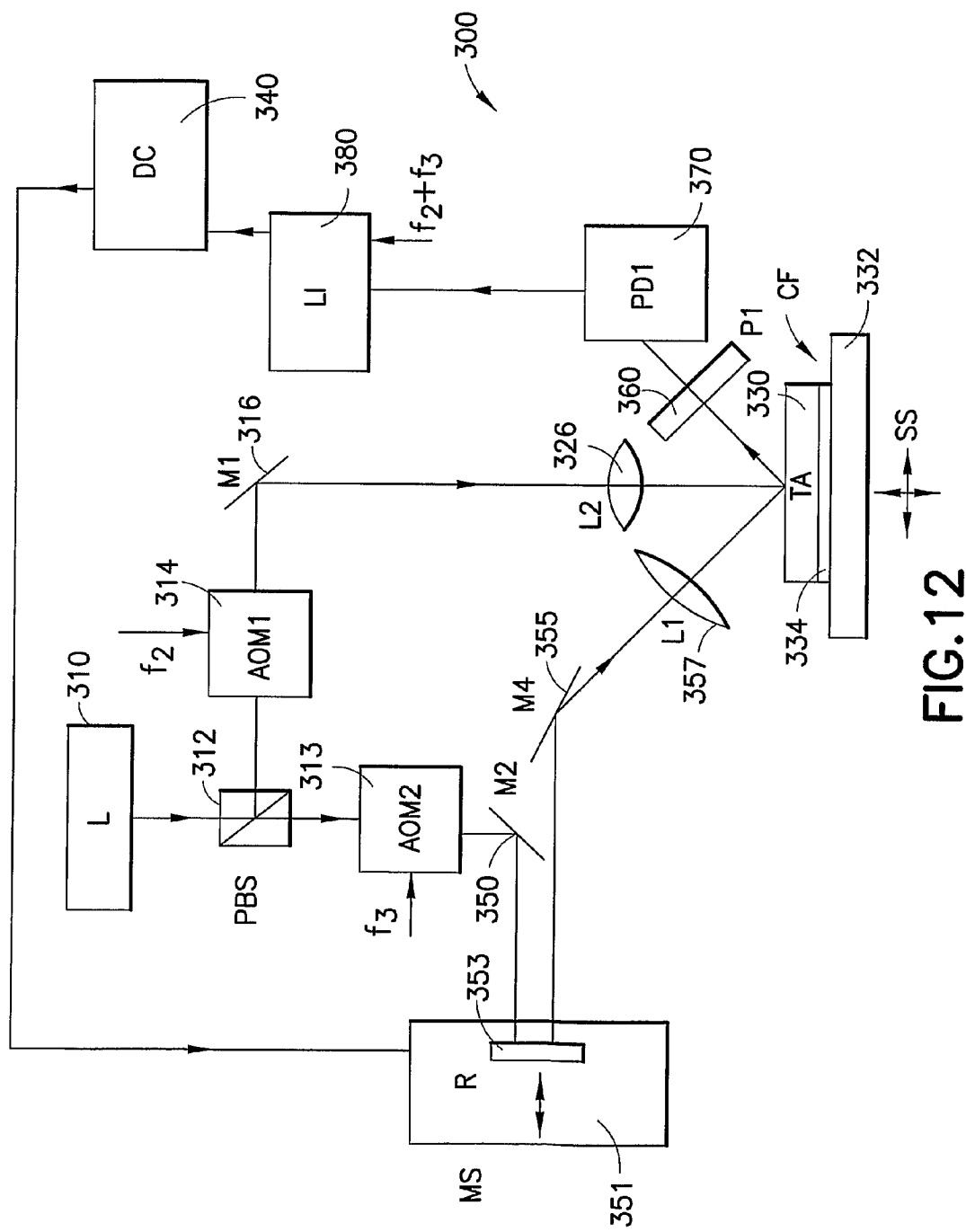
FIG. 12 is a schematic block diagram depicting a further scanning acoustic microscope having an opto-acoustic transducer assembly, all made in accordance with the present invention.

FIG. 12 shows another embodiment 300 that includes an acousto-optic modulator AOM2 that modulates the probe light pulses at a frequency $f_3$. The modulators AOM1 314 and AOM2 313 are driven at frequencies $f_2$ and $f_3$ by a frequency source not shown in the figure. This frequency source also provides a frequency $f_2+f_3$ to be used as the reference input for the lock-in amplifier 380. The advantage of modulating the amplitude of the probe as well as the pump is that the lock-in amplifier 380 rejects the signal arising from the part of the pump light that is scattered at the transducer assembly and then reaches the photodiode PD1 370. It is also within the scope of this invention to use a frequency $f_2-f_3$ as the reference input for the lock-in amplifier 380. It is within the scope of the invention to use electro-optic modulators in place of the acousto-optic modulators.

In the embodiment depicted in FIG. 12, a pulsed laser 310 generates a series of short light pulses. Each pulse is split into two by means of a polarizing beam splitter 312. As indicated previously, both the pump pulse and probe pulses are directed into acousto-optical modulators AOM1 314, AOM2 313 respectively, where AOM1 314 is driven at frequency $f_2$ and AOM2 is driven at frequency $f_3$. The pump pulses are then directed by mirror 316 to lens 326 which couples the light to the substrate of the opto-acoustic transducer assembly 330.

After the AOM2 313, the probe pulses are directed by mirror 350 to the reflector 353 mounted on movable stage 351. Each probe pulse is then directed by mirror 355 to lens L1 357 which focuses the light onto the opto-acoustic transducer assembly 330. The movable stage MS 351 is under the control of the digital computer DC 340, and is used to control the arrival time of the probe pulses at the transducer assembly TA 330.

After reflection by the layer of opto-acoustic material of the opto-acoustic transducer assembly 330, the probe pulses pass through the polarizer P1 360 and are then detected by the optical detector PD1 370. The polarizer 360 is oriented so as to block scattered pump light from reaching the detector 370. The output of this detector 370 is fed into the signal input of the lock-in amplifier L1 380. The demodulated output from the lock-in amplifier 380 is directed to the digital computer DC 340 for analysis. As indicated previously, the advantage of modulating the amplitude of the probe as well as the pump is that the lock-in amplifier 380 rejects the signal arising from the part of the pump light that is scattered at the transducer assembly and then reaches the photodiode PD1 370.

As in the case of the other embodiments, a sample is placed on a sample stage 332. The sample object is in turn coupled to the opto-acoustic transducer assembly 330 by a coupling fluid 334.

Figure 13:
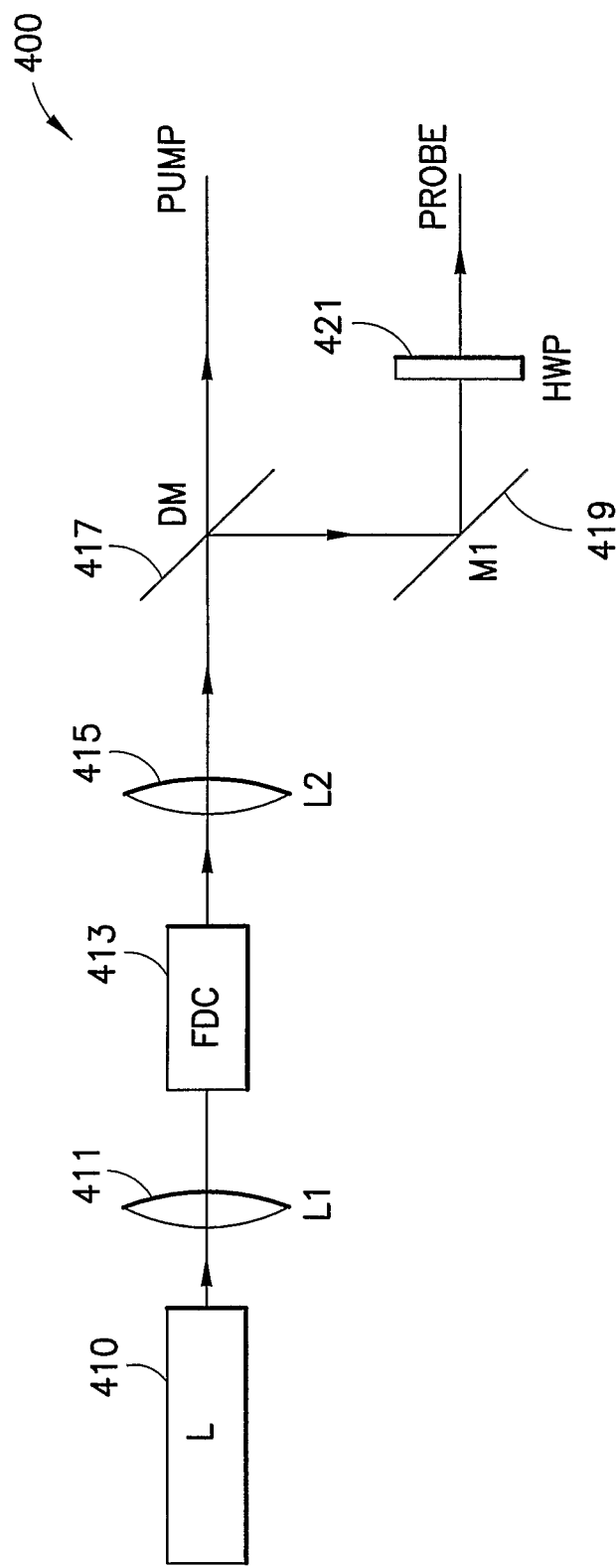
FIG. 13 is a schematic block diagram of yet another scanning acoustic microscope having an opto-acoustic transducer assembly, all made in accordance with the present invention.

FIG. 13 shows an embodiment of a scanning acoustic microscope 400 incorporating a frequency doubling crystal FDC 413. Light from the laser 410 is focused by lens L1 411 onto the frequency doubling crystal 413. The light pulses emerging from FDC 413 contain a component which has twice the frequency of the entering light. Lens L2 415 recollimates the light. Dichroic mirror DM 417 reflects the frequency doubled component of the light beam and transmits the undoubted component. The undoubted component is used for the pump pulses and the doubled component for the probe pulses. The half wave plate HWP 421 rotates the polarization of the probe by 90°. It is also within the scope of the invention to use a dichroic mirror that transmits the doubled component and reflects the undoubted component. It is also within the scope of the invention to use a dichroic mirror that transmits the doubled component and reflects the undoubted component. Under certain conditions, it may be advantageous to use frequency doubled light for both the pump and probe.

It is also within the scope of the invention to use separate lasers for the pump and the probe that are synchronized so that a probe light pulse is produced by one laser at a chosen time after each pump pulse is produced by the other laser. With this arrangement, the wavelengths of the pump and probe can be chosen to have optimal values. Specifically, the pump wavelength should be such as to maximize the amplitude of the generated sound pulse in the coupling fluid, and the probe wavelength chosen to maximize the change in the optical reflectivity of the transducer for a given amplitude of the sound pulse returning from the sample.

Figure 14:
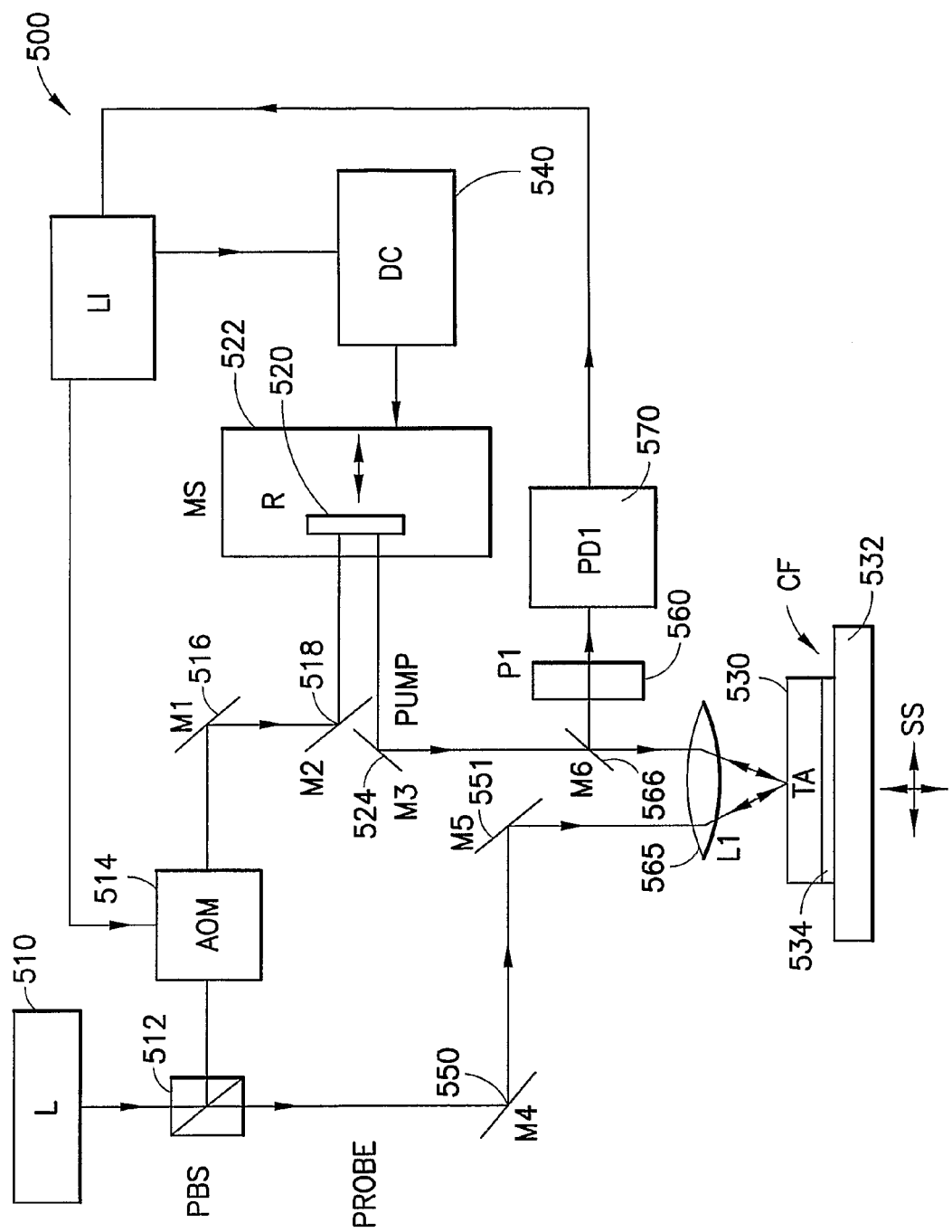
FIG. 14 is a schematic block diagram of a still further scanning acoustic microscope having an opto-acoustic transducer assembly, all made in accordance with the present invention.

FIG. 14 shows an embodiment of a scanning acoustic microscope 500 in which the same lens 565 is used to couple both the pump and the probe beams into the substrate of the opto-acoustic transducer assembly. The probe light is now directed by mirrors M4 550 and M5 551 to one side of the lens L1 565. After the probe light is reflected from the opto-acoustic transducer assembly 530 it passes through the other side of the lens 565 and part of it is reflected by mirror M6 566 to the photodiode PD1 570. Mirror M6 566 is partially transmitting and allows a fraction of the pump light to reach the sample through lens L1 565.

In these embodiments, some fraction of the laser light that reaches the ultrasonic transducer will be reflected back along an optical path that causes it to return and enter the laser. Depending on the type of laser that is used and the amount of light that is reflected back this returning light can have deleterious effects on the laser stability. To avoid this problem it is sufficient to incorporate a Faraday isolator into the optical path.

It may be convenient to use an optical fiber to carry the light over some sections of the optical path.

In addition to embodiments in which sound is generated by means of an opto-acoustic transducer and generated by the same or by a different opto-acoustic transducer, the invention further comprises embodiments in which:
a) sound is generated by other means, (for example, through the use of the piezo-electric effect), and after interacting with the sample object is detected by an opto-acoustic transducer;
b) sound is generated by an opto-acoustic transducer and after interacting with the sample object is detected by other means, (for example, through the use of the piezo-electric effect).

These embodiments may be advantageous for certain sample objects.

In addition to the apparatus set forth previously, the present invention also concerns methods for using an instrument having an opto-acoustic transducer assembly for generating high-frequency, low-wavelength sound waves useful for sensing the physical properties of a sample.

In one such method of the present invention, the instrument is used to measure the surface topography of a sample. In this application, the height of the surface of a solid would be measured as a function of lateral position. In one method for measuring the topography, the microscope lens can be scanned laterally across the surface of the solid, in raster fashion. The signal detected due to the return of the acoustic signal from the sample surface will depend on the height of the surface. In an alternate method, the microscope lens can be scanned laterally across the surface of the solid, in raster fashion in a similar manner to the first method. The signal detected due to the return of the acoustic signal from the sample surface will depend on the height of the surface, but in contrast to the first method, the height of the lens above the surface is adjusted so as to restore the detected signal to a reference value. The height of the lens will vary with lateral position in exactly the same way as the height of the surface.

In other embodiments of the methods of the present invention, an instrument is used to study the topography of layered structures. Consider, for example, a substrate that is covered by a thin film. The height of an opto-acoustic transducer operating in accordance with the present invention is first adjusted so that the sound is focused onto the upper (free) surface of the film. By performing a lateral scan of the opto-acoustic transducer the topography of this surface is determined. The height of the opto-acoustic transducer is then changed so that the sound is focused onto the interface between the substrate and the film. A lateral scan of the opto-acoustic transducer then gives the topography of this interface.

In operations in accordance with the present invention, acoustic waves penetrate into a sample object in addition to being reflected from it. The degree of penetration depends on the elastic properties of the sample. If the sample is a soft material, e.g., a polymer, with sound velocity and mass density in the same general range as water, then a substantial fraction of the energy of the acoustic wave will propagate across the water/sample interface. For a sample which has a very high sound velocity and/or a high density the transmission will be less. Because of this transmission of sound, instruments operating in accordance with the teachings of the present invention can be used to study the mechanical properties of the material near to the upper surface of a sample. For quantitative measurements, the amplitude S of the returning signal can be measured as a function of the height z of the transducer, of the time delay $t_{pp}$ of the probe pulse and of the frequency f. The dependence of S on z, $t_{pp}$ and f is then analyzed. The measured dependence of S can next be compared with a calculated dependence of S on z, $t_{pp}$ and f based on postulated values of the elastic properties of the sample object. Then, the assumed elastic properties can be adjusted until a good agreement between the calculated and measured results is obtained. The calculation of S can be performed using the finite-element method or other computational approach.

If a sample object is covered in whole or in part by a thin layer of a surface contaminant, a determination of the elastic properties of this thin layer may in certain circumstances make it possible to identify the nature of the contaminant, e.g., the chemical composition.

If the sample object is a solid, when the acoustic pulse from the microscope enters into the sample object Rayleigh surface waves are generated. These Rayleigh surface waves are very sensitive to cracks in the surface of the sample, and hence the presence of cracks shows up as a modification of the measured S. The higher the acoustic frequency the more sensitive the instrument is to small cracks, and thus for the detection of cracks the present invention will have a superior performance compared to conventional acoustic microscopes. Cracks can also be seen by impregnation with a fluorescent dye such as fluoresceine and then looking for fluorescence from these regions. However, acoustic microscopy has been shown to reveal cracks that are not seen by fluorescence techniques. (See, for example, "Acoustic Microscopy of Rocks", A. Rodriguez-Rey, G. A. D. Briggs, T. A. Field and M. Montoto, J. Microsc. 160, 21 (1990). It is also possible to study cracks that result from nanoindentation. ("Observation of Surface Cracks with an Acoustic Microscope", K. Yamanata and Y. Enomoto, J. Appl. Phys. 53, 846 (1982)).

Measurements can also be made for a sample consisting of a thin film deposited onto a substrate. The adhesion of the film to the substrate can be determined. In such a sample, the part of the acoustic pulse that enters into the film will travel across the film and reach the interface between the film and the substrate. At that interface, part of the pulse will be reflected back towards the upper surface of the films and then towards the acoustic transducer, and part will continue into the substrate. The amplitude of the reflected component will be dependent on the quality of the adhesion of the film to the substrate. If the adhesion is poor, the reflection will be larger. A scan across the surface of the sample can provide a map of the adhesion as a function of position. Previous studies of adhesion as a function of position have been-reported using the picosecond ultrasonic technique (see "Picosecond Ultrasonics Study of the Modification of Interfacial Bonding by Ion Implantation", G. Tas, J. J. Loomis, H. J. Maris, A. A. Bailes, and L. E. Seiberling, Applied Physics Letters 72, 2235 (1998)).

However, in that study a focused light pulse was used to directly excite sound waves in the thin film of the sample. As a consequence, the spatial resolution was limited, i.e., the light was focused to a spot of diameter approximately 20 microns. By an improved focusing system the size of the spot may be decreased to around 1 micron, but it would not be possible to achieve a focal diameter of better than 0.1 micron as is possible with the use of the exemplary embodiments of this invention. It is important to note that the exemplary embodiments in accordance with the invention focus sound instead of light, and the wavelength of the sound can be made significantly less than the wavelength of light.

The invention can also be used to study sample objects that are immersed within the water coupling medium (or other liquid). For example, the sample could be a biological cell adhering to a substrate. The invention could be used to determine the mechanical properties of different parts of the cell, or to determine the locations of different elements within the cell. Studies of this type have been performed with conventional acoustic microscopes ("Scanning acoustic microscopy visualizes cytomechanical responses to cytochalasin", J. Bereiter-Hahn, Journal of Microscopy 146, 29 (1987); "Acoustic microscopy of red blood cells", E. A. Schenk, R. W. Waag, A. B. Schenk and J. P. Aubuchon, Journal of Histochemistry and Cytochemistry 36, 1341 (1988); "Measurement of cellular elastic properties by acoustic microscopy", J. A. Hildebrand and D. Rugar, Journal of Microscopy 134, 245 (1984).)

Figure 15:
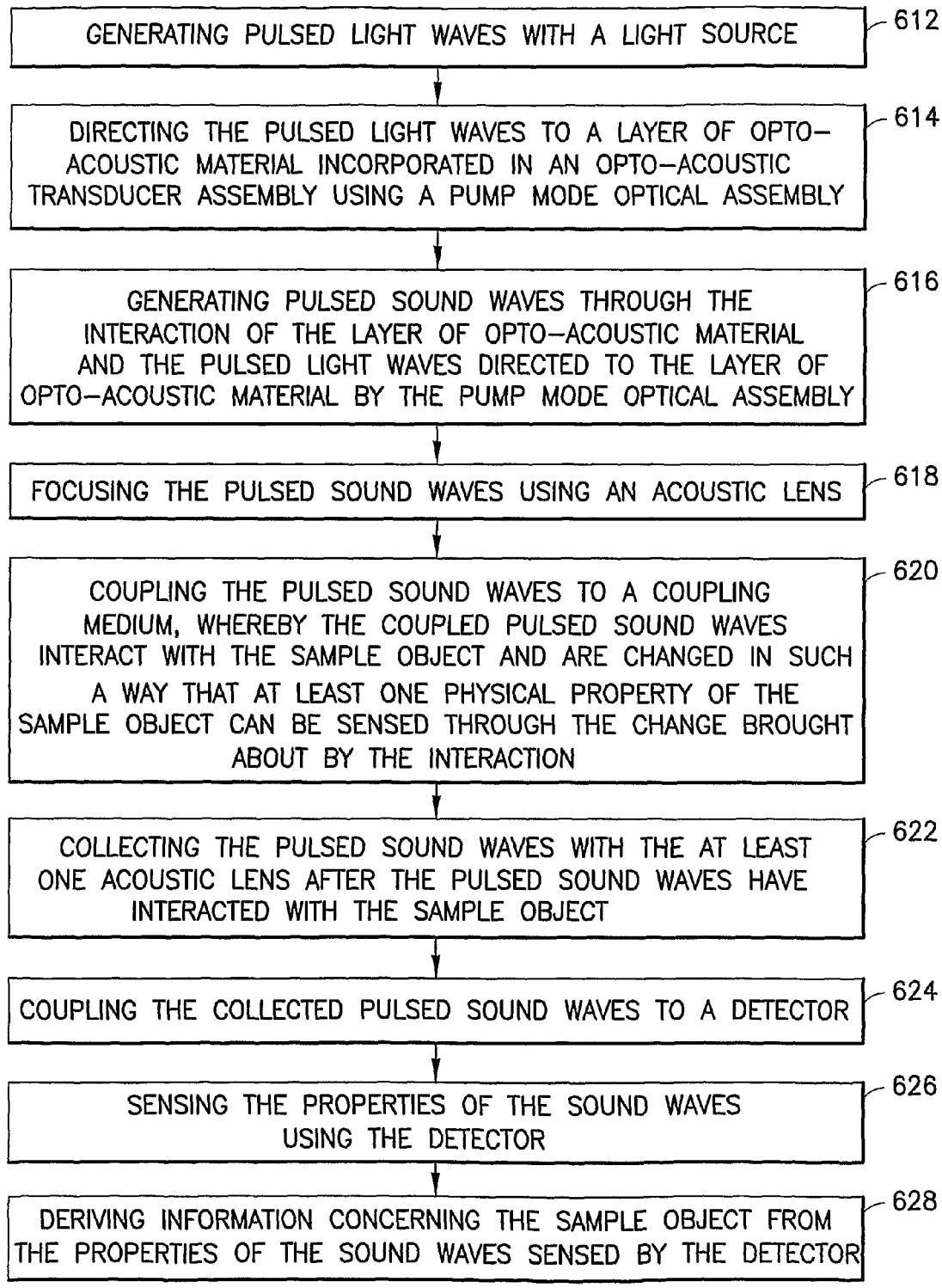
FIG. 15 is a flow chart depicting a method operating in accordance with the present invention.

In summary, general aspects of methods operating in accordance with the present invention for performing sample probing operations are set forth in the flow chart of FIG. 15. At step 612, pulsed light waves are generated by a light source. Then at step 614, the pulsed light waves are directed by a pump mode optical assembly to a layer of opto-acoustic material incorporated in an opto-acoustic transducer assembly operating in accordance with the present invention. Pulsed sound waves are generated at step 616 through the interaction of the layer of opto-acoustic material and the pulsed light waves directed to the layer of opto-acoustic material by the pump mode optical assembly. Next, at steps 618 and 620, the pulsed sound waves are focused and coupled to a coupling medium in which a sample object is immersed. After the pulsed sound waves have interacted with the sample object, the acoustic lens collects the pulsed sound waves at step 622. Then at step 624 the collected sound waves are coupled to a detector. Next, at step 626, the properties of the sound waves are sensed using the detector. Then, at step 628, information concerning the sample object is derived from the properties of the sound waves sensed by the detector.

In one variant of the method depicted in FIG. 15, a probe mode light source, the opto-acoustic transducer assembly and a probe mode optical assembly function as the detector in steps 624-628. In other variants of the method depicted in FIG. 15, a piezo-electric transducer assembly functions as the detector.

In still further variants, the method depicted in FIG. 15 operates in scanning and non-scanning modes. In scanning modes, the method is used to collect topographical information concerning a sample object. The topographical information may concern an uppermost surface of a sample object, or inner layers of a multi-layer structure.

An instrument operating in accordance with the method of FIG. 15 can be used both in scanning and non-scanning modes to measure the mechanical properties of a sample object.

As well as serving as a focused source of ultrasonic waves for microscopy imaging purposes, the opto-acoustic transducer in conjunction with the pump mode optical assembly has other applications as a focusing acoustic optic source. The following examples are cited but other applications will be apparent to those skilled in the art:

1) The high amplitude sound in the vicinity of the acoustic focus can be used as acoustical tweezers in the manner described by J. Wu, J. Acoust. Soc. Am. 89, 2140 (1991). In that work, frequencies in the MHz range were used giving an acoustic focus of large extent. With the opto-acoustic transducer of this invention, the diameter of the acoustic focus can be approximately 1000 times smaller and will be more effective for trapping very small objects, i.e., objects with dimensions in the range from about 100 ml down to about 1 nm.

2) The high amplitude sound in the vicinity of the focus can also be used for materials processing on the nanoscale. The following examples are cited but other applications will be apparent to those skilled in the art.

a) It is known that high amplitude sound can modify the chemical bonding in materials. V. I. Trigub and A. V. Plotnov (Technical Physics Letters, vol. 28, no. 6, June 2002. p. 8-10) have demonstrated this process by application of 21 kHz ultrasound to MMA-MAA copolymer photoresist. Through the use of the opto-acoustic transducer, it is possible to induce these modifications in chemical bonding in selected regions of material that have dimensions of the order of the acoustic focus, e.g., dimensions below 100 nm.

b) It is known that high amplitude sound can be used to implant atoms into metal surfaces (Y. Arata, Yue-Chang Zhang; Applied Physics Letters, vol. 80, no. 13, 1 Apr. 2002. p. 2416-18). Through the use of the opto-acoustic transducer, it is possible to perform this implantation in selected regions of material that have dimensions of the order of the acoustic focus, e.g., dimensions below 100 nm.

c) It is known that high amplitude sound can be used to modify the mechanical properties of a surface (I. V. Ostrovskii, L. P. Steblenko, A. B. Nadtochii, Semiconductors, vol. 34, no. 3, March 2000. p. 251-4). Through the use of the opto-acoustic transducer, it is possible to perform this modification in selected regions of material that have dimensions of the order of the acoustic focus, e.g., dimensions below 100 nm.

As the use of the exemplary embodiments of this invention can produce modifications of material properties in a selected region of material near to a surface, it may be used to repair defects on computer chips and to repair the masks that are used in computer chip fabrication. It can also be used to directly write patterns onto chips or onto masks.

Figure 16:
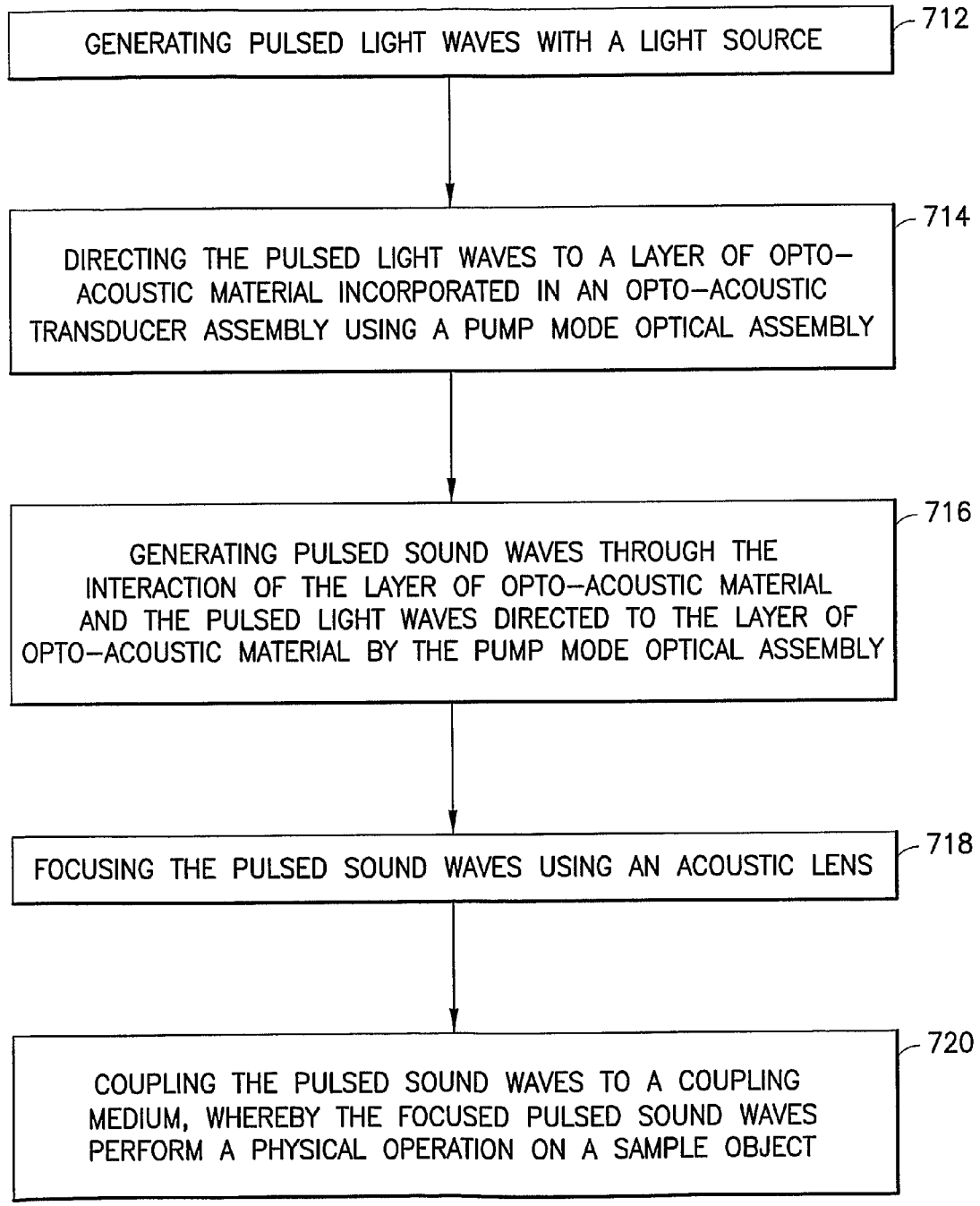
FIG. 16 is a flow chart depicting another method operating in accordance with the present invention.

In summary, general aspects of methods operating in accordance with the present invention for altering at least one physical property of a sample object are depicted in the flow chart of FIG. 16. At step 712, pulsed light waves are generated by a light source. Then at step 714 the pulsed light waves are directed by a pump mode optical assembly to a layer of opto-acoustic material incorporated in an opto-acoustic transducer assembly. Next, at step 716 pulsed sound waves are generated through the interaction of the layer of opto-acoustic material and the pulsed light waves directed to the layer of opto-acoustic material by the pump mode optical assembly. An acoustic lens focuses the pulsed sound waves at step 718. Then at step 720 the pulsed sound waves are coupled to a coupling medium, whereby the focused pulsed sound waves perform a physical operation on a sample object.

In variants of the method depicted in FIG. 16 various physical operations can be performed on a sample object. For example, in one variant an acoustic tweezers operation can be performed on a sample object. In other variants, repairs can be performed on masks used in semiconductor fabrication; semiconductor wafers; or semiconductor chips. In further variants patterns can be formed on masks used in semiconductor fabrication; semiconductor wafers; or semiconductor chips.

Figure 17:
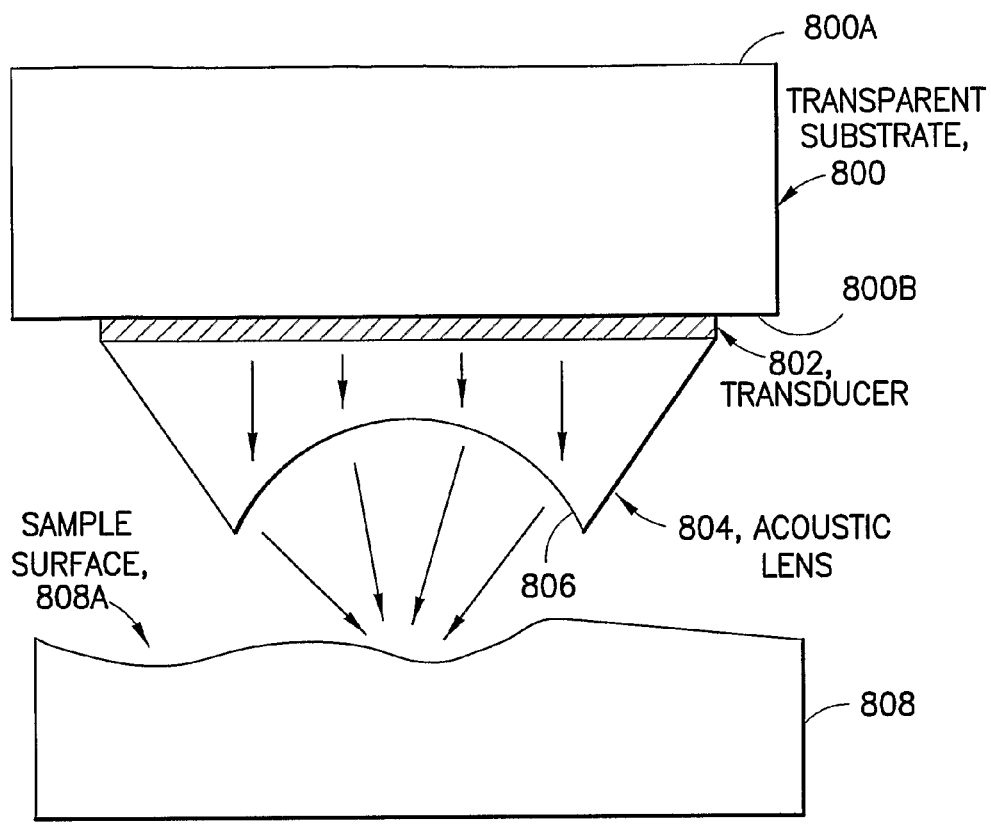
FIG. 17 depicts a further embodiment of an opto-acoustic transducer assembly made in accordance with the present invention.

A further opto-acoustic transducer assembly embodiment is shown in FIG. 17, which may also be incorporated in a scanning acoustic microscope for performing imaging operations, as one exemplary and non-limiting application and use. In the embodiment of FIG. 17 a transparent (at the optical wavelengths of interest) substrate 800, such as one made from aluminum oxide, has a transducer 802 deposited on a lower surface 800B thereof as a single layer or a multi-layer film structure. An acoustic lens 804 is fabricated on the surface of the transducer 802 film opposite the surface that abuts the substrate 800, the acoustic lens 804 including a concave semi-hemispherical or generally curved $SiO_2$ cavity 806. The acoustic lens 804 may be formed from, as non-limiting examples, or a polymer. The pump and probe light is incident on the top surface 800A of the substrate 800. In this embodiment the transducer 802 is interposed between the substrate 800 and the acoustic lens 804. Suitable and non-limiting thickness dimensions for the substrate 800 and the transducer 802 shown in FIG. 17 are 100 micrometers and 30 nanometers, respectively.

Figure 18:
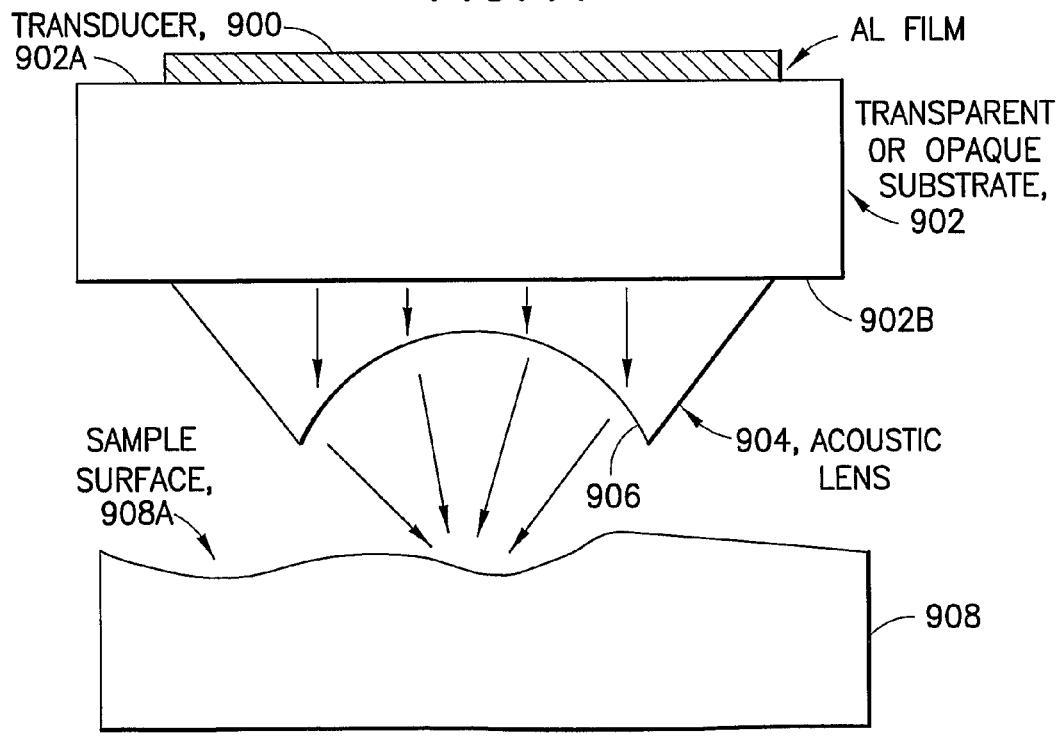
FIG. 18 depicts a further embodiment of an opto-acoustic transducer assembly made in accordance with the present invention.

It can be noted that the embodiments discussed thus far have referred to the use of a transparent substrate. Referring to FIG. 18 there is shown an embodiment of an acoustic transducer in which the transducer film 900 (e.g., an Al film) is disposed on a top surface 902A of a transparent or an opaque (at the optical wavelengths of interest) substrate 902. An acoustic lens 904 is fabricated on the bottom surface 902B of the substrate 902, the acoustic lens 904 including a concave semi-hemispherical or generally curved cavity 906. The acoustic lens 904 may be formed from, as non-limiting examples, $SiO_2$ or a polymer. In this embodiment, as may also be the case for certain of the other embodiments discussed above, the substrate 902 and the acoustic lens 904 may fabricated as one-monolithic body, or they may be separately fabricated and then joined together. The pump and probe light is incident on the top surface of the transducer film 900. Suitable and non-limiting thickness dimensions for the substrate 902 and the transducer 900 are 100 micrometers and 30 nanometers, respectively.

Figure 19:
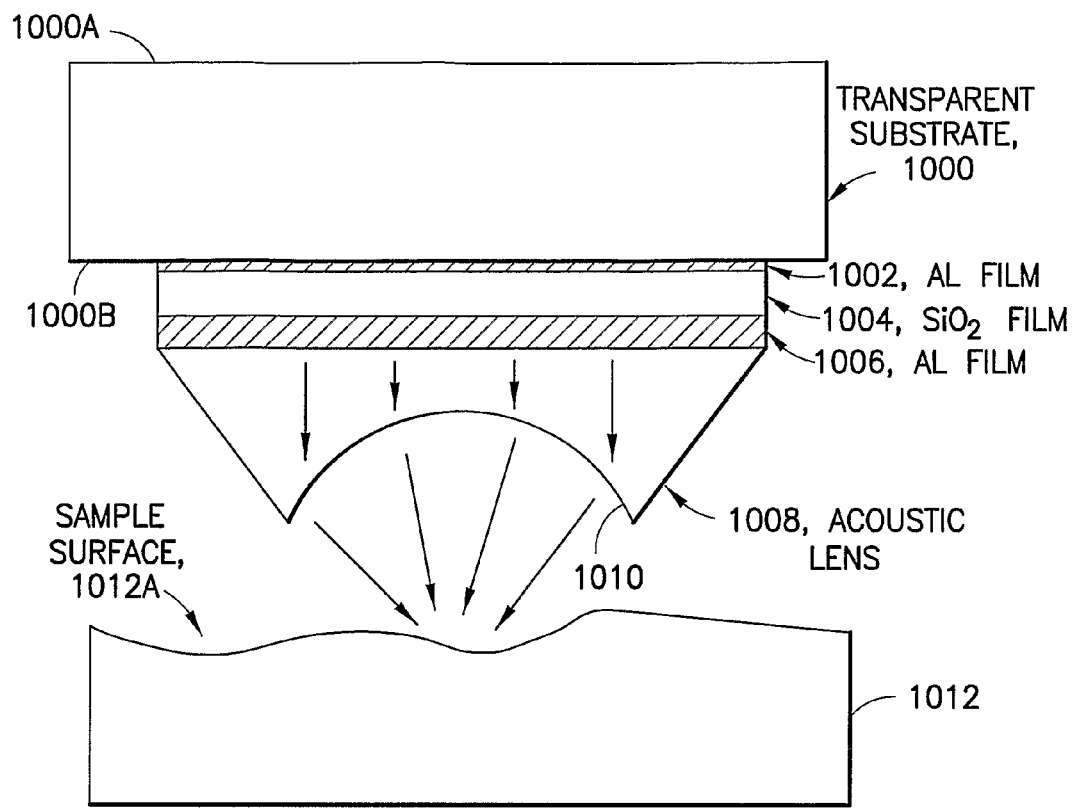
FIG. 19 depicts a further embodiment of an opto-acoustic transducer assembly made in accordance with the present invention.

For the purposes of detecting the returning sound pulse it may be advantageous to provide the transducer as a multi-layer structure as opposed to a single film layer. One non-limiting example is shown in FIG. 19. On the lower surface 1000B of the substrate 1000 are deposited, in sequence, films of a non-dielectric material, such as a metal (e.g., aluminum) 1002, a dielectric material (e.g. silicon dioxide or a polymer) 1004 and a second non-dielectric material such as the same or another metal 1006. The acoustic lens 1008 is located below the second non-dielectric film 1006, and the pump and probe light pulses are directed down from the top surface 1000A of the substrate 1000. The upper Al film 1002 is made sufficiently thin so as to transmit an appreciable fraction of the light pulses. Sound is generated when the pump light is absorbed in either or both of the Al films 1002, 1006. Probe light that passes through the upper Al film 1002 is reflected back and forth multiple times within the $SiO_2$ film 1004 between the upper and lower Al films, 1002, 1004, effectively setting up a standing wave. As may be appreciated, the Al/$SiO_2$/Al structure defined by films 1002, 1004, 1006 acts as a Fabry-Perot interferometer, or optical microcavity. If the thickness of the $SiO_2$ layer is appropriately chosen, the reflection of light from the Al/$SiO_2$/Al structure is very sensitive to small changes in the thickness and/or refractive index of the $SiO_2$ layer 1004. A returning sound pulse causes a change in the thickness of the $SiO_2$ layer 1004 and modifies the refractive index of the $SiO_2$ layer 1004. Thus when a sound pulse returns from the surface 1012A of the sample 1012 and enters the $SiO_2$ layer 1004, a large change occurs in the reflection of the probe light pulse. This type of structure thus provides a sensitive means for the detection of the returning sound pulses.

To fabricate the micro-cavity just described, the thickness of the $SiO_2$ layer 1004 is preferably made to be approximately equal to an integer number of half wavelengths of the probe light in the $SiO_2$. Thus, if the wavelength of the probe light in vacuum is 600 nm and the refractive index of the $SiO_2$ layer is 1.46, the thickness of the $SiO_2$ layer should be about 205 nm or 410 µm, etc.

It is noted that under the conditions just described the phase of the reflected probe light also undergoes a large (and detectable) change when sound travels through the $SiO_2$ layer 1004.

There are a number of possible and useful variations of this embodiment of the invention.

Figure 20:
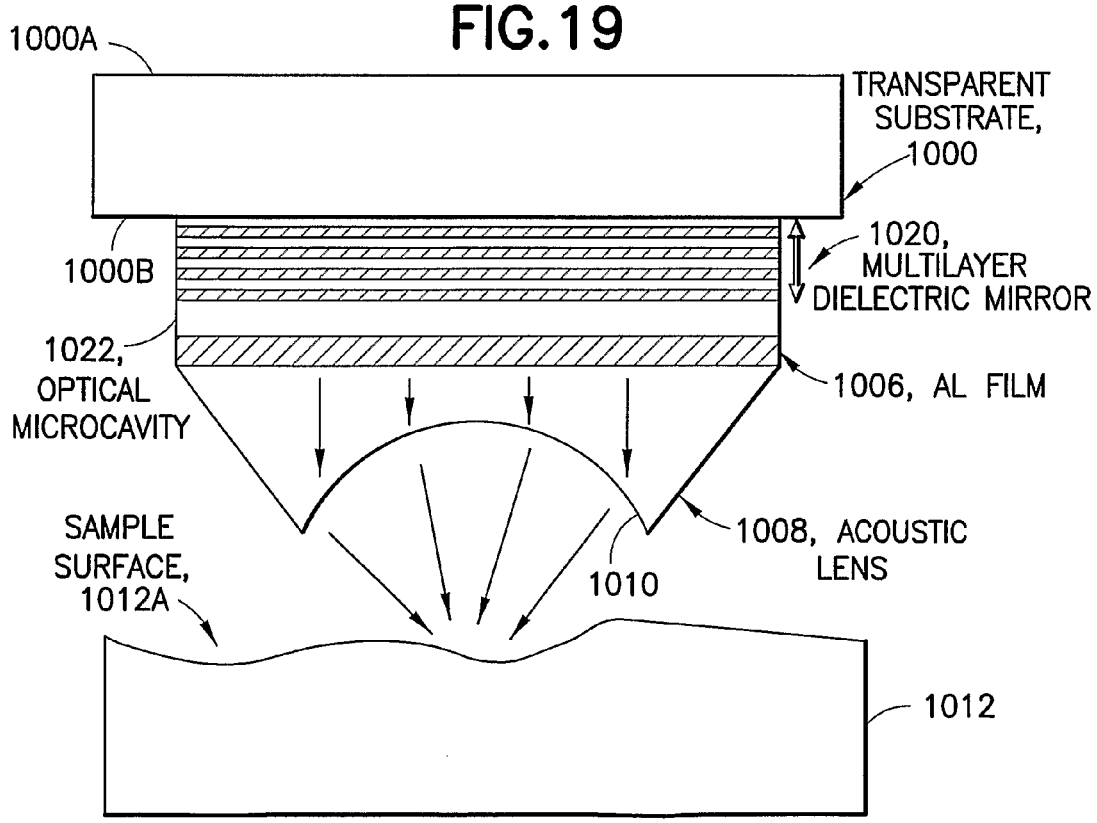
FIG. 20 depicts a still further embodiment of an opto-acoustic transducer assembly made in accordance with the present invention.

For example, the upper Al film 1002 may be replaced by a multilayer dielectric mirror structure 1020 as in FIG. 20. The multilayer dielectric mirror structure 1020 acts as a Bragg-type reflector for the incident light pulse(s). An optical microcavity layer 1022 disposed between the multilayer dielectric mirror structure 1020 and the Al film 1006 includes a layer of $SiO_2$, or other dielectric material, of appropriate thickness. When the returning sound pulse enters the optical microcavity layer 1022 it changes the thickness and refractive index of this layer. This results in a large change in the optical reflection of the overall structure consisting of the multilayer dielectric mirror structure 1020, optical micro-cavity layer 1022 and the Al film 1006. In practice, the multilayer dielectric mirror structure 1020 may have, as non-limiting examples, from 2 to 16 alternating dielectric films (e.g., $SiO_2$ and $TiO_2$). The film thicknesses and numbers of films are preferably tuned in relation to the probe beam wavelength. In addition to the change in the reflectivity due to the effect of the sound on the material in the optical micro-cavity, there will also be a contribution to the reflectivity change of the overall structure due to: 1) the change in the refractive index and thickness of the materials composing the multilayer dielectric mirror when the sound passes through the mirror and 2) the change in the optical properties and thickness of the Al film when the sound passes through the Al film.

The dielectric mirror structure 1020 is constructed so as to contain alternating layers of two materials 1 and 2 with different refractive indices $n_1$ and $n_2$. In the embodiment shown in FIG. 20, the thickness of each layer of material 1 is the same throughout the structure, and the thickness of each layer of material 2 is also the same throughout the structure. However, it may be advantageous to use a dielectric mirror structure 1020 in which the thickness of each of the layers of material 1 (and each of material 2) is different. For example, the thickness of each successive layer of material 1 could be larger than the thickness of the preceding layer by a selected amount. In this way, it is possible to construct a dielectric mirror that yields a larger change in the reflectivity of the overall structure as a result of the arrival of the sound pulse.

It is noted that by using different wavelengths for the pump and probe light pulses it is possible to make the multilayer dielectric mirror structure 1020 have different transmission and reflection characteristics for the pump and probe light pulses.

For the purpose of generating and detecting the returning sound pulse it may be advantageous to use a laterally patterned film or films, with individual structural features possessing dimensions which are less than the wavelength of light employed. For example, and referring to FIG. 21, such a film may include an array of metal dots 1050 surrounded by dielectric material 1052, or an array of dots 1060 composed of dielectric material filling apertures in a metal film 1062, or other finely nano-textured materials with size in the range of, for example, 1 nm to 100 nm. As non-limiting embodiments, the metal in FIGS. 21 and 22 may include, Al, Au or As, while the dielectric material may include a polymer or an oxide. The dot structures 1050, 1060 can be formed using micro-nano-fabrication techniques such as those based on electron-beam lithography, through the use of self-assembled arrays of nanoparticles such as quantum dots, or by conventional photolithographic techniques, and may include as examples etching and backfilling etched voids with a metal or a dielectric, or may include an implantation process. Such a patterned film can be prepared so as to have a reflection and absorption coefficient that has a favorable value for use with the invention. A returning sound pulse operates to change the optical properties of the metal and the dielectric components of the film, and the change in the optical reflection induced by the returning sound pulse can be made to have a large value. The structure can be also designed for optimizing the absorption of incident optical pump light at specific wavelengths so as to enhance the generation of the acoustic pulses. As non-limiting examples the dots can be made to have a height of 100 nm or less, and a diameter of 100 nm or less.

Thus it is seen that the foregoing description has provided by way of exemplary and non-limiting examples a full and informative description of the exemplary embodiments of this invention for performing, as non-limiting examples, high resolution imaging and other sample probing operations using opto-acoustic principles. One skilled in the art will appreciate that the various embodiments described herein can be practiced individually; in combination with one or more other embodiments described herein; or in combination with scanning acoustic microscopes and other instruments differing from those described herein. Further, one skilled in the art will appreciate that the present invention can be practiced by other than the described embodiments; that these described embodiments are presented for the purposes of illustration and not of limitation; and that the present invention is not limited to only the specific embodiments disclosed above.

What is claimed is:

1. An opto-acoustic transducer assembly comprising:
   a substrate;
   at least one layer of opto-acoustic material coupled to a surface of the substrate, where the at least one layer of opto-acoustic material generates sound waves when struck by light; and
   an acoustic lens to focus sound waves generated by the at least one layer of opto-acoustic material, and
   where said at least one layer of opto-acoustic material is interposed between said substrate and said acoustic lens, and where said substrate is substantially transparent to light having wavelengths of interest.

2. The opto-acoustic transducer assembly of claim 1 where the acoustic lens comprises a concave cavity.

3. The opto-acoustic transducer assembly of claim 2 where the concave cavity is semi-hemispherical, whereby sound waves generated by the at least one layer of opto-acoustic material when struck by light are focused substantially to a point focus by the acoustic lens.

4. The opto-acoustic transducer assembly of claim 2 where the concave cavity is partially cylindrical, whereby sound waves generated by the at least one layer of opto-acoustic material when struck by light are focused substantially to a line focus by the acoustic lens.

5. The opto-acoustic transducer assembly of claim 1 where the at least one layer of opto-acoustic material is deposited on a surface of the substrate.

6. The opto-acoustic transducer assembly of claim 1 where the opto-acoustic material comprises $As_2Te_3$.

7. The opto-acoustic transducer assembly of claim 1 where the at least one layer of opto-acoustic material vibrates after being struck by a single pulse of light of predetermined characteristics for a predetermined number of cycles at a predetermined frequency before damping out, where the predetermined number of cycles is dependent upon respective acoustic impedances of the at least one layer of opto-acoustic material and the substrate.

8. The opto-acoustic transducer assembly of claim 7 where the predetermined frequency is at least 15 GHz.

9. The opto-acoustic transducer assembly of claim 7 where the predetermined number of cycles is between about 2 and about 10.

10. The opto-acoustic transducer assembly of claim 1 where the substrate comprises sapphire.

11. The opto-acoustic transducer assembly of claim 1, where said at least one layer of opto-acoustic material is comprised of a layer of dielectric material that is interposed between two metal layers.

12. The opto-acoustic transducer assembly of claim 11, where a thickness of said layer of dielectric material is a function of a wavelength of light used to detect sound waves collected by said acoustic lens that return from a sample.

13. The opto-acoustic transducer assembly of claim 1, where said at least one layer of opto-acoustic material is comprised of a multilayer stack of first layers comprised of a first dielectric material that alternate with second layers comprised of a second dielectric material.

14. The opto-acoustic transducer assembly of claim 13, where a thickness of said multilayer stack is a function of a wavelength of light used to detect sound waves collected by said acoustic lens that return from a sample.

15. The opto-acoustic transducer assembly of claim 1, where said at least one layer of opto-acoustic material is comprised of a laterally patterned film.

16. The opto-acoustic transducer assembly of claim 15, where said laterally patterned film is comprised of metal-containing structures embedded in a dielectric material.

17. The opto-acoustic transducer assembly of claim 15, where said laterally patterned film is comprised of dielectric structures embedded in a metal-containing film.

18. An opto-acoustic transducer assembly comprising:
a substrate;
at least one layer of opto-acoustic material coupled to a surface of the substrate, where the at least one layer of opto-acoustic material generates sound waves when struck by light; and
an acoustic lens to focus sound waves generated by the at least one layer of opto-acoustic material,
where the acoustic lens of the opto-acoustic transducer assembly is operative to collect sound waves originally generated by the at least one layer of opto-acoustic material after the sound waves have interacted with a sample object, and where at least one property of the at least one layer of opto-acoustic material changes in response to the collected sound waves, and
where the at least one layer of opto-acoustic material and the acoustic lens are formed on opposite sides of the substrate.

19. An opto-acoustic transducer assembly comprising:
a substrate, said substrate being substantially transparent to light having wavelengths of interest; and
at least one layer of opto-acoustic material coupled to a surface of the substrate, where the at least one layer of opto-acoustic material generates sound waves when struck by light, and where the at least one layer of opto-acoustic material is deposited on the surface of the substrate in a plurality of non-contiguous concentric rings, whereby the non-contiguous concentric rings are an acoustic lens which focuses a sound wave substantially to a point focus.

20. The opto-acoustic transducer assembly of claim 19 where the layer of opto-acoustic material is formed from at least one of GaN; InGaN; Cr.

21. The opto-acoustic transducer assembly of claim 19 where a central region defined by an innermost ring of opto-acoustic material is substantially transparent and functions as a sub-wavelength optical aperture for a near-field optical microscope.

22. The opto-acoustic transducer assembly of claim 19 where the plurality of non-contiguous concentric rings is formed from multiple layers deposited on the surface of the substrate.

23. The opto-acoustic transducer assembly of claim 22 where one of the multiple layers comprises GaN.

24. The opto-acoustic transducer assembly of claim 22 where one of the multiple layers comprises InGaN.

25. The opto-acoustic transducer assembly of claim 22 where one of the multiple layers comprises Cr.

26. An opto-acoustic transducer assembly comprising:
a substrate, said substrate being substantially transparent to light having wavelengths of interest; and
at least one layer of opto-acoustic material coupled to a surface of the substrate, where the at least one layer of opto-acoustic material generates sound waves when struck by light, and where the at least one layer of opto-acoustic material is deposited on the surface of the substrate in a plurality of non-contiguous parallel strips, whereby the non-contiguous parallel strips are an acoustic lens which focuses sound waves substantially to a line focus.

27. An opto-acoustic transducer assembly comprising:
a substrate;
at least one layer of opto-acoustic material coupled to a surface of the substrate, where the at least one layer of opto-acoustic material generates sound waves when struck by light; and
an acoustic lens to focus sound waves generated by the at least one layer of opto-acoustic material,
where the acoustic lens of the opto-acoustic transducer assembly is operative to collect sound waves originally generated by the at least one layer of opto-acoustic material after the sound waves have interacted with a sample object, and where at least one property of the at least one layer of opto-acoustic material changes in response to the collected sound waves.

28. The opto-acoustic transducer assembly of claim 27 where the at least one property is at least one of the reflectivity of the opto-acoustic material, the refractive index of the opto-acoustic material, and a dimension of the opto-acoustic material.

29. The opto-acoustic transducer assembly of claim 27 whereby the change in a property of the layer of opto-acoustic material caused by sound waves impinging the layer of opto-acoustic material in turn changes at least one of a following property of light of predetermined characteristics impinging the layer of opto-acoustic material: an intensity of the light; a phase of the light; a direction of the light; a polarization of the light.

30. The opto-acoustic transducer assembly of claim 27, where said substrate is interposed between said at least one layer of opto-acoustic material and said acoustic lens.

31. An opto-acoustic transducer assembly comprising:
a substrate;
at least one layer of opto-acoustic material coupled to a surface of the substrate, where the at least one layer of opto-acoustic material generates sound waves when struck by light; and
an acoustic lens to focus sound waves generated by the at least one layer of opto-acoustic material,
where the opto-acoustic transducer assembly comprising, in part, at least one layer of opto-acoustic material which generates sound waves when struck by light comprises a first opto-acoustic transducer assembly, the first opto-acoustic transducer assembly operating in combination with:
a second opto-acoustic transducer assembly, where the second opto-acoustic transducer assembly is operative to collect sound waves originally generated by the first opto-acoustic transducer assembly after the sound waves have interacted with a sample object, the second opto-acoustic transducer assembly comprising:
a second substrate;
at least one second layer of opto-acoustic material formed on a surface of the second substrate whereby when sound waves impinge the at least one second layer of opto-acoustic material at least one property of the opto-acoustic material changes; and
a second acoustic lens.

32. The opto-acoustic transducer assembly of claim 31 where the property of the second layer of opto-acoustic material which changes is at least one of the reflectivity of the opto-acoustic material, the refractive index of the opto-acoustic material, and a dimension of the opto-acoustic material.

33. The opto-acoustic transducer assembly of claim 31 where the change in a property of the at least one second layer of opto-acoustic material caused by sound waves impinging the at least one second layer of opto-acoustic material in turn changes at least one of a following property of light of predetermined characteristics impinging the at least one second layer of opto-acoustic material: an intensity of the light; a phase of the light; a direction of the light; a polarization of the light.

34. A transducer assembly for use in an instrument which is in turn used to probe a sample object, the transducer assembly having dual piezo-electric and opto-acoustic modes of operation, the transducer assembly comprising:
 a substrate;
 a layer of opto-acoustic material deposited on a surface of the substrate, the layer of opto-acoustic material being electrically conductive;
 a layer of piezo-electric material deposited on the layer of opto-acoustic material;
 a layer of electrically conductive material deposited on the layer of piezo-electric material;
 an acoustic lens; and
 whereby when a pulsed electric potential is applied between the layer of opto-acoustic material and the layer of conductive material, a pulsed electric field is created which causes the layer of piezo-electric material to deform and thereby create pulsed sound waves which are focused by the acoustic lens and then used to probe the sample object, and whereby after the pulsed sound waves interact with the sample object and are collected by the acoustic lens, the collected pulsed sound waves impinge the layer of opto-acoustic material thereby changing at least one optical property of the layer of opto-acoustic material.

35. A scanning acoustic microscope comprising:
 at least one light source for generating pulsed light used at least in a pump mode to generate pulsed sound waves to interact with a sample object to be probed using the pulsed sound waves; and
 at least one opto-acoustic transducer assembly comprising:
 a substrate;
 at least one layer of opto-acoustic material coupled to a surface of the substrate, where the at least one layer of opto-acoustic material generates pulsed sound waves when struck by the pulsed light generated by the at least one light source;
 an acoustic lens to focus pulsed sound waves generated by the at least one layer of opto-acoustic material, and
 a probe mode optical assembly for coupling pulsed light generated by the at least one light source to the at least one opto-acoustic transducer assembly, where the pulsed light generated by the at least one light source coupled to the at least one opto-acoustic transducer assembly by the probe mode optical assembly is used to sense a change in at least one property of the at least layer of opto-acoustic material caused by sound waves after they have interacted with a sample object being probed by the scanning acoustic microscope.

36. The scanning acoustic microscope as in claim 35 further comprising: a pump mode optical assembly for coupling the pulsed light generated by the at least one light source to the opto-acoustic transducer assembly, where the pulsed light coupled to the opto-acoustic transducer assembly by the pump mode optical assembly is used to generate sound waves to interact with the sample object; and
 a computer control for controlling the operation of the scanning acoustic microscope.

37. The scanning acoustic microscope of claim 36 where the scanning acoustic microscope operates in a reflection mode, where pulsed sound waves are returned from the sample object back to the at least one opto-acoustic transducer assembly, and where the scanning acoustic microscope further comprises:
 a beam splitter for splitting pulsed light generated by the at least one light source, where resulting component pulsed light beams are coupled to the pump mode optical assembly and the probe mode optical assembly, respectively.

38. The scanning acoustic microscope of claim 36 where the scanning acoustic microscope operates in a reflection mode, and where:
 the at least one light source comprises a first and second light source, where the first light source generates pulsed light for coupling to the pump mode optical assembly and where the second light source generates pulsed light for coupling to the probe mode optical assembly.

39. The scanning acoustic microscope of claim 38 where the first light source coupled to the pump mode optical assembly is optimized for operation with the at least one layer of opto-acoustic material to generate pulsed sound waves.

40. The scanning acoustic microscope of claim 38 where the second light source coupled to the probe mode optical assembly is optimized for operation with the at least one layer of opto-acoustic material to measure changes in at least one property of the at least one layer of opto-acoustic material caused by sound waves impinging the layer of opto-acoustic material.

41. The scanning acoustic microscope of claim 36 where the scanning acoustic microscope operates in a transmission mode, and where:
 the at least one opto-acoustic transducer assembly further comprises a first and second opto-acoustic transducer assembly, where the first opto-acoustic transducer assembly is coupled to the pump mode optical assembly and generates pulsed sound waves for interacting with the sample object to be probed by the scanning acoustic microscope and where the second opto-acoustic transducer assembly is coupled to the probe mode optical assembly, where the pulsed light coupled to the second opto-acoustic transducer assembly by the probe mode optical assembly is used to sense the change of an optical property of the at least one layer of opto-acoustic material when pulsed sound waves transmitted by the sample object impinge the opto-acoustic material.

42. The scanning acoustic microscope of claim 41 where:
 the at least one light source further comprises a first and second light source, where the first light source generates pulsed light for coupling to the pump mode optical assembly and where the second light source generates pulsed light for coupling to the probe mode optical assembly.

43. The scanning acoustic microscope of claim 42 where the first light source coupled to the pump mode optical assembly is optimized for operation with the at least one layer of opto-acoustic material to generate pulsed sound waves.

44. The scanning acoustic microscope of claim 42 where the second light source coupled to the probe mode optical assembly is optimized for operation with the at least one layer of opto-acoustic material to measure changes in an optical property of the at least one layer of opto-acoustic material caused by sound waves impinging the at least one layer of opto-acoustic material.

45. The scanning acoustic microscope of claim 36 further comprising: a pump mode modulation means for modulating an amplitude of the pump mode pulsed light prior to the pump mode pulsed light impinging the layer of opto-acoustic material of the opto-acoustic transducer assembly.

46. The scanning acoustic microscope of claim 45 where the pump mode modulation means comprises an electro-optic modulator.

47. The scanning acoustic microscope of claim 45 where the pump mode modulation means comprises an acousto-optic modulator.

48. The scanning acoustic microscope of claim 45 further comprising: a photodetector for detecting the probe mode pulsed light waves after the probe mode pulsed light waves have interacted with the at least one layer of opto-acoustic material of the opto-acoustic transducer assembly, and further comprising: a lock-in amplifier coupled to an output of the photodetector and an input of the pump mode modulation means for controlling the pump mode modulation means in dependence upon a signal received from the photodetector.

49. The scanning acoustic microscope of claim 45 where the pump mode modulation means operates at a first frequency, the probe mode optical assembly further comprising: a probe mode modulation means for modulating the amplitude of the probe mode pulsed light at a second frequency different from the first frequency used to modulate the pump mode pulsed light, the modulation of the probe mode pulsed light occurring prior to the probe mode pulsed light impinging the layer of opto-acoustic material of the opto-acoustic transducer assembly.

50. The scanning acoustic microscope of claim 49 where the probe mode modulation means comprises an electro-optic modulator.

51. The scanning acoustic microscope of claim 49 where the pump mode modulation means comprises an acousto-optic modulator.

52. The scanning acoustic microscope of claim 36 where the pump mode optical assembly further comprises a reflector mounted on a movable stage, where the movable stage is coupled to the computer control and is operative to control a difference in arrival times between pump mode pulsed light and probe mode pulsed light at the opto-acoustic transducer assembly.

53. The scanning acoustic microscope of claim 36 where the probe mode optical assembly further comprises a reflector mounted on a movable stage, where the movable stage is coupled to the computer control and is operative to control a difference in arrival times between pump mode pulsed light and probe mode pulsed light at the opto-acoustic transducer assembly.

54. The scanning acoustic microscope of claim 36 further comprising: a frequency-doubling crystal for creating a frequency component at twice a nominal frequency of the light source prior to the coupling of the pulsed light to the pump and probe mode optical assemblies.

55. The scanning acoustic microscope of claim 54 further comprising: a dichroic mirror that transmits a frequency component of pulsed light at the nominal frequency of the at least one light source to the pump mode optical assembly and reflects the component at twice the nominal frequency to the probe mode optical assembly.

56. The scanning acoustic microscope of claim 55 further comprising: a half-wave plate for rotating a polarization of the probe mode pulsed light coupled to the probe mode optical assembly by the dichroic mirror.

57. The scanning acoustic microscope of claim 54 further comprising: a dichroic mirror that transmits a frequency component of pulsed light at the nominal frequency of the at least one light source to the probe mode optical assembly and reflects the component at twice the nominal frequency to the pump mode optical assembly.

58. The scanning acoustic microscope of claim 35 where the at least one property is at least one of the reflectivity of the opto-acoustic material, the refractive index of the opto-acoustic material, and a dimension of the opto-acoustic material.

59. The scanning acoustic microscope of claim 35 whereby the change in at least one property of the at least one layer of opto-acoustic material caused by sound waves impinging the at least one layer of opto-acoustic material in turn changes at least one of a following property of light of predetermined characteristics impinging the layer of opto-acoustic material: an intensity of the light; a phase of the light; a direction of the light; a polarization of the light.

60. The scanning acoustic microscope of claim 35 further comprising a coupling fluid for coupling the sound waves generated by the opto-acoustic transducer assembly to the sample object.

61. The scanning acoustic microscope of claim 35 further comprising: a photodetector for detecting the probe mode pulsed light waves after the probe mode pulsed light waves have interacted with the at least one layer of opto-acoustic material of the opto-acoustic transducer assembly.

62. The scanning acoustic microscope of claim 61 further comprising: a polarizer for preventing scattered pump-mode light pulses from reaching the photodetector.

63. The scanning acoustic microscope of claim 35 further comprising: a near-field optical microscope, whereby the scanning acoustic microscope and near-field optical microscope provide dual, optic and acoustic, modes of operation.

64. The scanning acoustic microscope of claim 35 where the layer of opto-acoustic material is deposited on the surface of the substrate in a plurality of non-contiguous concentric rings, and whereby the non-contiguous concentric rings further comprise the acoustic lens, and where a central region formed by an innermost ring of opto-acoustic material is transparent and functions as a sub-wavelength optical aperture for a near-field optical microscope, the scanning acoustic microscope further comprising: the near-field optical microscope, whereby the scanning acoustic microscope and near-field optical microscope provide dual, optic and acoustic, modes of operation.

65. The scanning acoustic microscope of claim 35 further comprising: a piezo-electric transducer assembly, where the piezo-electric transducer assembly is operative to collect pulsed sound waves originally generated by the opto-acoustic transducer assembly after the pulsed sound waves have interacted with the sample object, the piezo-electric transducer assembly comprising:
a substrate;
a layer of piezo-electric material formed on a surface of the substrate, at least one electrical property of the layer of piezo-electric material changing when pulsed sound waves impinge the layer of piezo-electric material;
an acoustic lens formed on or in the substrate to collect the pulsed sound waves originally generated by the opto-acoustic transducer assembly after the pulsed sound waves have interacted with the sample object; and
means to measure the change in the at least one electrical property of the layer of piezo-electric material.

66. A scanning acoustic microscope comprising:
a piezo-electric transducer assembly comprising:
a substrate;
a layer of piezo-electric material formed on a surface of the substrate which generates pulsed sound waves to interact with a sample object to be probed with the pulsed sound waves when a voltage is applied to the layer of piezo-electric material;

an acoustic lens formed on or in the substrate to focus the pulsed sound waves;

a voltage source coupled to the layer of piezo-electric material;

at least one opto-acoustic transducer assembly, where the opto-acoustic transducer assembly is operative to collect pulsed sound waves originally generated by the piezo-electric transducer assembly after the pulsed sound waves have interacted with the sample object, the opto-acoustic transducer assembly comprising:

a substrate;

a layer of opto-acoustic material formed on a surface of the substrate, where a property of the layer of opto-acoustic material changes when pulsed sound waves collected by the opto-acoustic transducer assembly impinge the layer of opto-acoustic material;

an acoustic lens to collect pulsed sound waves generated by the piezo-electric transducer assembly after the pulsed sound waves have interacted with the sample object;

at least one light source for generating pulsed light, where the pulsed light will be used at least in a probe mode to measure the change in a property of the layer of opto-acoustic material caused by the pulsed sound waves collected by the opto-acoustic transducer assembly impinging on the layer of opto-acoustic material after the pulsed sound waves have interacted with the sample object;

a probe mode optical assembly for coupling the pulsed light generated by the at least one light source to the opto-acoustic transducer assembly;

a table for mounting the sample object to be probed; and a computer control for controlling the operation of the scanning acoustic microscope.

67. A method for sensing physical properties of a sample object, comprising:

providing an instrument having at least one opto-acoustic transducer assembly;

generating first pulsed light waves with a light source;

directing the first pulsed light waves to at least one layer of opto-acoustic material incorporated in the at least one opto-acoustic transducer assembly;

generating pulsed sound waves through the interaction of the at least one layer of opto-acoustic material and the first pulsed light waves;

focusing the pulsed sound waves using an acoustic lens and directing them to the sample object to interact with the sample object in such a way that at least one physical property of the sample object can be sensed through the change brought about by the interaction;

collecting the pulsed sound waves with the acoustic lens after the pulsed sound waves have interacted with the sample object; and deriving information concerning the sample object from collected sound waves, where the at least one layer of opto-acoustic material is interposed between the acoustic lens and a substrate to which the first pulse light waves are directed, and where said substrate is substantially transparent to light having wavelengths of interest.

68. The method of claim 67 where collecting comprises sensing a change in at least one of the reflectivity, the refractive index and a dimension of a material due to the collected sound waves.

69. The method of claim 67 where the method further comprises:

scanning the opto-acoustic transducer assembly in two dimensions across a surface of the sample object to collect information from sample points.

70. The method of claim 69 where the information comprises height information about the surface of the sample object at particular (x,y) co-ordinates on the surface of the sample object.

71. The method of claim 70 where the height information is determined by adjusting the height of the opto-acoustic transducer assembly.

72. The method of claim 69 where the information comprises mechanical properties of the sample object.

73. The method of claim 69 where the information comprises a presence of or an absence of cracks in the sample object.

74. A method to perform a physical operation on a sample object, comprising:

providing at least one opto-acoustic transducer assembly comprising a substrate, a layer of opto-acoustic material and an acoustic lens, where the layer of opto-acoustic material is coupled to a first surface of the substrate and is interposed between the first surface of the substrate and the acoustic lens;

generating pulsed light waves with a light source;

directing the pulsed light waves to a second surface of the substrate opposite the first surface and through the substrate to the layer of opto-acoustic material;

generating pulsed sound waves through the interaction of the layer of opto-acoustic material and the pulsed light waves;

focusing the pulsed sound waves using the acoustic lens;

coupling the pulsed sound waves to the sample object through a coupling medium, where the focused pulsed sound waves perform a physical operation on the sample object.

75. The method of claim 74 where the physical operation is an acoustic tweezers operation.

76. The method of claim 74 where the sample object is a mask used in semiconductor fabrication and where the physical operation comprises a modification of the mask.

77. The method of claim 74 where the sample object is a mask used in semiconductor fabrication and where the physical operation comprises forming a pattern on the mask.

78. The method of claim 74 where the sample object is a semiconductor wafer and the physical operation comprises a modification of the semiconductor wafer.

79. The method of claim 74 where the sample object is a semiconductor wafer and the physical operation comprises forming a pattern on the semiconductor wafer.

80. The method of claim 74 where the sample object is a semiconductor chip and the physical operation comprises a modification of the semiconductor chip.

81. The method of claim 74 where the sample object is a semiconductor chip and the physical operation comprises forming a pattern on the semiconductor chip.

82. An opto-acoustic transducer assembly comprising:

a substrate having a top surface for receiving pump light and probe light and a bottom surface;

a transducer coupled to the bottom surface, said transducer generating sound waves in response to the pump light; and an acoustic lens coupled to said transducer to focus the generated sound waves towards a sample and to collect sound waves returning from the sample;

where said transducer is comprised of a layer of dielectric material that is interposed between two non-dielectric layers, and where a thickness of said layer of dielectric material is a function of at least a wavelength of the probe light and is modifiable by collected sound waves to cause a detectable change in the probe light.

83. An opto-acoustic transducer assembly comprising:
a substrate having a top surface for receiving pump light and probe light and a bottom surface;
a transducer coupled to the bottom surface, said transducer generating sound waves in response to the pump light; and
an acoustic lens coupled to said transducer to focus the generated sound waves towards a sample and to collect sound waves returning from the sample;
where said transducer is comprised of an optical micro-cavity layer that is interposed between a metal-containing layer and a multi-layered dielectric stack, and where a thickness of said optical micro-cavity layer is a function of a wavelength of at least the probe light and is modifiable by collected sound waves to cause a detectable change in the probe light.

84. The opto-acoustic transducer assembly of claim 83, where said multi-layered dielectric stack comprises alternating layers of a first material and a second material having different refractive indices, where a thickness of each layer of said first material is the same throughout the multi-layered dielectric stack and where a thickness of each layer of said second material is the same throughout the multi-layered dielectric stack.

85. The opto-acoustic transducer assembly of claim 83, where said multi-layered dielectric stack comprises alternating layers of a first material and a second material having different refractive indices, where a thickness of each successive layer of said first material is greater than a thickness of a preceding layer of said first material by a predetermined amount, and where a thickness of each successive layer of said second material is greater than a thickness of a preceding layer of said second material by a predetermined amount.

86. The opto-acoustic transducer assembly of claim 83, where said pump light has a first wavelength, where said probe light has a second wavelength that differs from the first wavelength, and where said multi-layered dielectric stack exhibits different transmission and reflection characteristics for the pump light and the probe light.

87. An opto-acoustic transducer assembly comprising:
a substrate having a top surface for receiving light and a bottom surface;
a transducer coupled to the bottom surface, said transducer generating sound waves in response to the light; and
an acoustic lens coupled to said transducer to focus the generated sound waves towards a sample and to collect sound waves returning from the sample;
where the transducer is comprised of at least one laterally patterned layer having individual structural features possessing dimensions that are less than the wavelength of light employed.

* * * * *